US012567492B1

(12) United States Patent
Chudova et al.

(10) Patent No.: US 12,567,492 B1
(45) Date of Patent: Mar. 3, 2026

(54) GENETIC VARIANT DETECTION BASED ON MERGED AND UNMERGED READS

(71) Applicant: GUARDANT HEALTH, INC., Palo Alto, CA (US)

(72) Inventors: Darya Chudova, Los Altos, CA (US); Mohammad Reza Mokhtari, San Lorenzo, CA (US)

(73) Assignee: Guardant Health, Inc., Palo Alto, CA (US)

( * ) Notice: Subject to any disclaimer, the term of this patent is extended or adjusted under 35 U.S.C. 154(b) by 0 days.

(21) Appl. No.: 19/020,482

(22) Filed: Jan. 14, 2025

Related U.S. Application Data

(63) Continuation of application No. 16/559,465, filed on Sep. 3, 2019, now abandoned.

(60) Provisional application No. 62/726,131, filed on Aug. 31, 2018.

(51) Int. Cl.
| | |
|---|---|
| *G16H 20/10* | (2018.01) |
| *G16B 5/10* | (2019.01) |
| *G16B 20/20* | (2019.01) |
| *G16B 30/10* | (2019.01) |

(52) U.S. Cl.
CPC .............. *G16H 20/10* (2018.01); *G16B 5/10* (2019.02); *G16B 20/20* (2019.02); *G16B 30/10* (2019.02)

(58) Field of Classification Search
None
See application file for complete search history.

(56) References Cited

U.S. PATENT DOCUMENTS

| | | | |
|---|---|---|---|
| 4,988,617 | A | 1/1991 | Landegren et al. |
| 5,242,794 | A | 9/1993 | Whiteley et al. |
| 5,494,810 | A | 2/1996 | Barany et al. |
| 5,648,245 | A | 7/1997 | Fire et al. |
| 5,952,170 | A | 9/1999 | Stroun et al. |
| 6,210,891 | B1 | 4/2001 | Nyren et al. |
| 6,306,597 | B1 | 10/2001 | Macevicz |
| 6,492,121 | B2 | 12/2002 | Kurane et al. |
| 6,582,908 | B2 | 6/2003 | Fodor et al. |
| 6,582,938 | B1 | 6/2003 | Su et al. |
| 6,586,177 | B1 | 7/2003 | Shuber |
| 6,828,100 | B1 | 12/2004 | Ronaghi |
| 6,833,246 | B2 | 12/2004 | Balasubramanian |
| 6,849,403 | B1 | 2/2005 | Shuber |
| 6,911,345 | B2 | 6/2005 | Quake et al. |
| 7,163,789 | B2 | 1/2007 | Chen et al. |
| 7,232,656 | B2 | 6/2007 | Balasubramanian et al. |
| 7,410,764 | B2 | 8/2008 | Gocke et al. |
| 7,537,898 | B2 | 5/2009 | Bost et al. |
| 7,598,035 | B2 | 10/2009 | Macevicz |
| 7,727,720 | B2 | 6/2010 | Dhallan |
| 7,811,757 | B2 | 10/2010 | Shuber |
| 7,824,889 | B2 | 11/2010 | Vogelstein et al. |

| | | | |
|---|---|---|---|
| 7,835,871 | B2 | 11/2010 | Kain et al. |
| 7,838,647 | B2 | 11/2010 | Hahn et al. |
| 7,915,015 | B2 | 3/2011 | Vogelstein et al. |
| 7,935,487 | B2 | 5/2011 | Gocke et al. |
| 7,937,225 | B2 | 5/2011 | Mishra et al. |
| 7,960,120 | B2 | 6/2011 | Rigatti et al. |
| 8,603,749 | B2 | 12/2013 | Gillevet |
| 8,685,678 | B2 | 4/2014 | Casbon et al. |
| 9,018,365 | B2 | 4/2015 | Brenner |
| 9,340,830 | B2 | 5/2016 | Lipson et al. |
| 9,404,156 | B2 | 8/2016 | Hicks et al. |
| 9,598,731 | B2 | 3/2017 | Talasaz |
| 9,850,523 | B1 | 12/2017 | Chudova et al. |
| 9,902,992 | B2 | 2/2018 | Talasaz et al. |
| 2001/0053519 | A1 | 12/2001 | Fodor et al. |
| 2002/0072058 | A1 | 6/2002 | Voelker et al. |
| 2003/0152490 | A1 | 8/2003 | Trulson et al. |
| 2006/0024681 | A1 | 2/2006 | Smith et al. |
| 2006/0073506 | A1 | 4/2006 | Christians et al. |
| 2006/0292611 | A1 | 12/2006 | Berka et al. |
| 2007/0065823 | A1 | 3/2007 | Dressman et al. |
| 2007/0114362 | A1 | 5/2007 | Feng et al. |
| 2008/0161420 | A1 | 7/2008 | Shuber |
| 2009/0026082 | A1 | 1/2009 | Rothberg et al. |
| 2009/0105959 | A1 | 4/2009 | Braverman et al. |
| 2009/0202999 | A1 | 8/2009 | Morley |
| 2010/0069250 | A1 | 3/2010 | White et al. |
| 2010/0196898 | A1 | 8/2010 | Sugarbaker et al. |
| 2010/0300559 | A1 | 12/2010 | Schultz et al. |

(Continued)

FOREIGN PATENT DOCUMENTS

| | | |
|---|---|---|
| EP | 1647600 A2 | 6/2006 |
| EP | 3169804 A1 | 5/2017 |

(Continued)

OTHER PUBLICATIONS

Parikh HI. MeFit: merging and filtering tool for illumina paired-end reads for 16S rRNA amplicon sequencing. BMC Bioinformatics 17:491, 6 pgs. (Year: 2016).*

Thomas A. From targets to targeted therapies and molecular profiling in non-small cell lung carcinoma. Annals of Oncology 24: 577-585. (Year: 2013).*

Layer RM. LUMPY: a probabilistic framework for structural variant discovery. Genome Biology 15: R84, 19 pgs. (Year: 2014).*

Alkan, et al. Personalized copy number and segmental duplication maps using next-generation sequencing. Nat Genet. Oct. 2009;41(10):1061-7. doi: 10.1038/ng.437. Epub Aug. 30, 2009.

Atanur, et al. The genome sequence of the spontaneously hypertensive rat: Analysis and functional significance. Genome Res. Jun. 2010;20(6):791-803. doi: 10.1101/gr.103499.109. Epub Apr. 29, 2010.

(Continued)

*Primary Examiner* — Olivia M. Wise
*Assistant Examiner* — Robert J. Kallal
(74) *Attorney, Agent, or Firm* — Timothy A. Hott

(57) ABSTRACT

Methods and systems for improving identification of nucleic acid variants by identifying genetic sequence reads having identical molecular barcodes and sequences among sequence reads from a nucleic acid sequencer, grouping the genetic reads into a family, and processing families comprising split reads to detect the variants in a sample of polynucleotide molecules.

19 Claims, 10 Drawing Sheets

(56) References Cited

U.S. PATENT DOCUMENTS

| | | | |
|---|---|---|---|
| 2010/0300895 A1 | 12/2010 | Nobile et al. | |
| 2010/0301398 A1 | 12/2010 | Rothberg et al. | |
| 2010/0304982 A1 | 12/2010 | Hinz et al. | |
| 2010/0323348 A1 | 12/2010 | Hamady et al. | |
| 2011/0009278 A1 | 1/2011 | Kain et al. | |
| 2011/0160078 A1 | 6/2011 | Fodor et al. | |
| 2011/0201507 A1 | 8/2011 | Rava et al. | |
| 2011/0245482 A1 | 10/2011 | Hahn et al. | |
| 2012/0316074 A1 | 12/2012 | Saxonov | |
| 2013/0005585 A1 | 1/2013 | Anderson et al. | |
| 2013/0022977 A1 | 1/2013 | Lapidus et al. | |
| 2013/0210643 A1 | 8/2013 | Casbon et al. | |
| 2013/0224743 A1 | 8/2013 | Casbon et al. | |
| 2013/0237458 A1 | 9/2013 | Casbon et al. | |
| 2013/0267424 A1 | 10/2013 | Casbon et al. | |
| 2014/0011694 A1 | 1/2014 | Couronne | |
| 2014/0222443 A1 | 8/2014 | Danenberg et al. | |
| 2014/0296081 A1 | 10/2014 | Diehn et al. | |
| 2014/0336943 A1 | 11/2014 | Pellini et al. | |
| 2015/0024950 A1 | 1/2015 | Bielas et al. | |
| 2015/0044687 A1 | 2/2015 | Schmitt et al. | |
| 2015/0087535 A1 | 3/2015 | Patel | |
| 2015/0142328 A1 | 5/2015 | Jung et al. | |
| 2015/0329917 A1 | 11/2015 | Shuber | |
| 2015/0344970 A1 | 12/2015 | Vogelstein et al. | |
| 2015/0366866 A1 | 12/2015 | Ali et al. | |
| 2016/0032396 A1 | 2/2016 | Diehn et al. | |
| 2016/0232291 A1 | 8/2016 | Kyriazopoulou-Panagiotopoulou et al. | |
| 2016/0246922 A1* | 8/2016 | Putnam .................. | G16B 30/00 |
| 2017/0051347 A1 | 2/2017 | Vogelstein et al. | |
| 2017/0073774 A1 | 3/2017 | Lo et al. | |
| 2017/0145516 A1 | 5/2017 | Kopetz et al. | |
| 2017/0159120 A1 | 6/2017 | Eijk et al. | |
| 2018/0237837 A1 | 8/2018 | Osborne et al. | |
| 2018/0251848 A1 | 9/2018 | Diehn et al. | |
| 2019/0185910 A1 | 6/2019 | Li et al. | |
| 2019/0241974 A1 | 8/2019 | Woodhouse et al. | |
| 2019/0241975 A1 | 8/2019 | Woodhouse et al. | |
| 2019/0241977 A1 | 8/2019 | Woodhouse et al. | |
| 2019/0241978 A1 | 8/2019 | Woodhouse et al. | |
| 2020/0058372 A1 | 2/2020 | Kim et al. | |
| 2020/0211675 A1 | 7/2020 | Filippova et al. | |
| 2021/0295947 A1 | 9/2021 | Kyriazopoulou-Panagiotopoulou et al. | |
| 2022/0033885 A1 | 2/2022 | Osborne et al. | |
| 2023/0178184 A1 | 6/2023 | Putnam et al. | |

FOREIGN PATENT DOCUMENTS

| | | | | |
|---|---|---|---|---|
| EP | 3125936 B1 | 5/2019 | | |
| WO | 2000058516 A2 | 10/2000 | | |
| WO | 2011087760 A2 | 7/2011 | | |
| WO | 2011091046 A1 | 7/2011 | | |
| WO | 2012014877 A1 | 2/2012 | | |
| WO | 2013019075 A2 | 2/2013 | | |
| WO | 2013142389 A1 | 9/2013 | | |
| WO | 2014028771 A1 | 2/2014 | | |
| WO | 2014039556 A1 | 3/2014 | | |
| WO | WO-2017062970 A1 * | 4/2017 | ............. | C12Q 1/686 |
| WO | 2018064629 A1 | 4/2018 | | |
| WO | 2018213814 A1 | 11/2018 | | |

OTHER PUBLICATIONS

Becker, T. et al. "FusorSV: an algorithm for optimally combining data from multiple structural variation detection methods" Genome Biology (2018) 19(38), https://doi.org/10.1186/s13059-018-1404-6.

Bonaldo, et al. Normalization and subtraction: two approaches to facilitate gene discovery. Genome Res. Sep. 1996;6(9):791-806.

Carr, et al. Inferring relative proportions of DNA variants from sequencing electropherograms. Bioinformatics. Dec. 15, 2009;25(24):3244-50. doi: 10.1093/bioinformatics/btp583. Epub Oct. 9, 2009.

Castle, et al. DNA copy number, including telomeres and mitochondria, assayed using next-generation sequencing. BMC Genomics. Apr. 16, 2010; 11:244. doi: 10.1186/1471-2164-11-244.

Chang, et al. Detection of allelic imbalance in ascitic supernatant by digital single nucleotide polymorphism analysis. Clin Cancer Res. Aug. 2002;8(8):2580-5.

Chen, K. et al. "BreakDancer: an algorithm for high-resolution mapping of genomic structural variation" Nature Methods (2009) 6:677-681.

Clark, T.A. et al. "Analytical Validation of a Hybrid Capture Based Next-Generation Sequencing Clinical Assay for Genomic Profiling of Cell-Free Circulating Tumor DNA," J. Mol. Diagnostics (2018) 20(5):686-702.

Costello, et al. Discovery and characterization of artifactual mutations in deep coverage targeted capture sequencing data due to oxidative DNA damage during sample preparation. Nucleic Acids Res. Apr. 1, 2013;41(6):e67. doi: 10.1093/nar/gks1443. Epub Jan. 8, 2013.

Daines, et al. High-throughput multiplex sequencing to discover copy number variants in *Drosophila*. Genetics. Aug. 2009; 182(4):935-41. doi: 10.1534/genetics.109.103218. Epub Jun. 15, 2009.

Exam Report for European Patent Application No. 19769350.0, dated Jul. 4, 2024.

Fan, et al. Non-invasive prenatal measurement of the fetal genome. Nature. Jul. 19, 2012;487(7407):320-4. doi: 10.1038/nature 11251.

Gelfand, Y. et al. "VNTRseek—a computational tool to detect tandem repeat variants in high-throughput sequencing data" NAR (2014) 42(14):8884-8894.

Grant, et al. SNP genotyping on a genome-wide amplified DOP-PCR template. Nucleic Acids Res. Nov. 15, 2002;30 (22):e25.

Greer, S.U. et al. "Linked read sequencing resolves complex genomic rearrangements in gastric cancer metastases" Genome Med (2017) 9(1):57.

Gundry, et al. "Direct mutation analysis by high-throughput sequencing: from germline to low-abundant, somatic variants" Mutat Res Jan. 3, 2012; 729(1-2):1-15. doi: 10.1016/mrfmmm.2011.10.001. Pub Oct. 12, 2011.

Gundry, et al. Direct, genome-wide assessment of DNA mutations in single cells. Nucleic Acids Res. Mar. 2012;40(5):2032-40. doi: 10.1093/nar/gkr949. Epub Nov. 15, 2011.

Hamady, et al. Error-correcting barcoded primers for pyrosequencing hundreds of samples in multiplex. Nat Methods. Mar. 2008;5(3):235-7. doi: 10.1038/nmeth. 1184. Epub Feb. 10, 2008.

Hensel, et al. Simultaneous identification of bacterial virulence genes by negative selection. Science. Jul. 21, 1995;269(5222):400-3.

Hiatt, et al. Single molecule molecular inversion probes for targeted, high-accuracy detection of low-frequency variation. Genome Res. May 2013;23(5):843-54. doi: 10.1101/gr.147686.112. Epub Feb. 4, 2013.

International Search Report and Written Opinion for PCT Application No. PCT/US2019/049382 dated Dec. 20, 2019.

Koboldt, et al. Massively parallel sequencing approaches for characterization of structural variation. Aug. 12, 2011. Methods Mol Biol. 2012;838:369-84. doi: 10.1007/978-1-61779-507-7_18.

Kremer, F.S. et al. "Approaches for in silico finishing of microbial genome sequences" Genetics and Mol Bio (2017) 40(3):553-576.

Kwon, S. et al. "CASPER: context-aware scheme for paired-end reads from high-throughput amplicon seqencing" BMC Bioinformatics (2014) 15(Suppl 9):S10 (11 pages).

Lam, HY et al. "Nucleotide-resolution analysis of structural variants using BreakSeq and a breakpoint library" Nature Biotech (2010) 28(1):47-55.

Lanman, et al., Analytical and Clinical Validation of a Digital Sequencing Panel for Quantitative, Highly Accurate Evaluation of Cell-Free Circulating Tumor DNA PloS One, Oct. 2015, 10(10), e0140712. doi: 10.1371/journal.pone.0140712.

Layer, et al.; LUMPY: A Probabilistic Framework for Structural Variant Discovery; Genome Biology; 2014; pp. 1-19.

Li et al. "SOAP: Short Oligonucleotide Alignment Program" Bioinformatics, 2008, vol. 24. pp. 713-714.

(56)          References Cited

OTHER PUBLICATIONS

Li, et al. Mapping short DNA sequencing reads and calling variants using mapping quality scores. Genome Res. Nov. 2008;18(11):1851-8. doi: 10.1101/gr.078212.108. Epub Aug. 19, 2008.

Li, et al., The Sequence Alignment/Map format and SAMtools, Bioinformatics, 2009, 25(16):2078-9.

Li, H. et al. "A survey of sequence alignment algorithms for next-generation sequencing" Briefings in Bioinformatics (2010) 2(5):473-483.

Lizardi, et al. Mutation detection and single-molecule counting using isothermal rolling-circle amplification. Nat Genet. Jul. 1998;19(3):225-32.

Makrigiorgos, et al., A PCR-Based amplification method retaining quantative difference between two complex genomes. Nature Biotech, vol. 20, No. 9, pp. 936-939 (Sep. 2002).

Marco-Sola, S. "Efficient Approximate String Matching Techniques for Sequence Alignment" Thesis, Universitat Politecnica de Catalunya (2017).

Mcpherson, A. et al. "DeFuse: An Algorithm for Gene Fusion Discovery in Tumor RNA-Seq Data" PLoS Computational Biology (May 19, 2011) 7(5):1-16.

Medvedev, et al. Detecting copy number variation with mated short reads. Genome Res. Nov. 2010;20(11):1613-22. doi: 10.1101/gr.106344.110. Epub Aug. 30, 2010.

Mei, et al. Identification of recurrent regions of Copy-Number Variants across multiple individuals. BMC Bioinformatics. Mar. 22, 2010;11:147. doi: 10.1186/1471-2105-11-147.

Mills, et al. "An initial map of insertion and deletion (INDEL) variation in the human genome" Genome Research (2006) 16(9):1182-1190.

Newman, et al. An ultrasensitive method for quantitating circulating tumor DNA with broad patient coverage. Nat Med. May 2014;20(5):548-54. doi: 10.1038/nm.3519. Epub Apr. 6, 2014.

Ning, Z. et al. "SSAHA: A Fast Search Method for Large DNA Databases" Genome Res (2001) 11:1725-1729.

Odegaard, J.I. et al. "Validation of a Plasma-Based Comprehensive Cancer Genotyping Assay Utilizing Orthogonal Tissue- and Plasma-Based Methodologies" Clin Canc Res (2018) 24(15):3539-3549.

Ogino, et al. Quantification of PCR bias caused by a single nucleotide polymorphism in SMN gene dosage analysis. J Mol Diagn. Nov. 2002;4(4):185-90.

Park, et al. Discovery of common Asian copy number variants using integrated high-resolution array CGH and massively parallel DNA sequencing. Nat Genet. May 2010;42(5):400-5. doi: 10.1038/ng.555. Epub Apr. 4, 2010.

Paweletz, C.P. et al. "Bias-corrected targeted next-generation sequencing for rapid, multiplexed detection of actionable alterations in cell-free DNA from advanced lung cancer patients" Clin Canc Res (2016) 22(4):915-922.

Phallen, J. et al. "Direct detection of early-stage cancers using circulating tumor DNA" Sci Trans Med (2017) vol. 9, Issue 403, eaan2415DOI: 10.1126/scitranslmed.aan2415.

Pleasance, et al. A small-cell lung cancer genome with complex signatures of tobacco exposure. Nature. Jan. 14, 2010;463(7278):184-90. doi: 10.1038/nature08629. Epub Dec. 16, 2009.

Rothberg, et al., An integrated semiconductor device enabling non-optical genome sequencing, Nature, 2011, 475:348-52.

Schroder, J. et al. "Socrates: Identification of Genomic Rearrangements in Tumour Genomes by Re-aligning Soft Clipped Reads" Bioinformatics (Jan. 2, 2014) 30(8):1064-1072.

Simpson, et al. Copy number variant detection in inbred strains from short read sequence data. Bioinformatics. Feb. 15, 2010;26(4):565-7. doi: 10.1093/bioinformatics/btp693. Epub Dec. 18, 2009.

Tan, et al. Genome-wide comparison of DNA hydroxymethylation in mouse embryonic stem cells and neural progenitor cells by a new comparative hMeDIP-seq method. Nucleic Acids Res. Apr. 2013;41(7):e84. doi: 10.1093/nar/gkt091. Epub Feb. 13, 2013.

Taudien, et al. Haplotyping and copy number estimation of the highly polymorphic human beta-defensin locus on 8p23 by 454 amplicon sequencing. BMC Genomics. Apr. 19, 2010; 11:252. doi: 10.1186/1471-2164-11-252.

Thieme, S. et al. "Genome Fusion Detection: a Novel Method to Detect Fusion Genes from SNP-Array Data" Bioinformatics (Jan. 22, 2013) 29(6):671-677.

Tomaz, et al. Differential methylation as a cause of allele dropout at the imprinted GNAS locus. Genet Test Mol Biomarkers. Aug. 2010; 14(4):455-60. doi: 10.1089/gtmb.2010.0029.

Tucker, T. et al. "Massively Parallel Sequencing: The Next Big Thing in Genetic Medicine" J Hum Genet (2009) 85:142-154.

Van De Paer, C. et al. "Mitogenomics of Hesperelaea, an extinct genus of *Oleaceae*" Gene (2016) 594(2):197-202.

Villaflor, V. et al. "Biopsy-free circulating tumor DNA assay identifies actionable mutations in lung cancer" Oncotarget (2016) 7(41):66880-66891.

Walker, et al. Isothermal in vitro amplification of DNA by a restriction enzyme/DNA polymerase system. Proc Natl Acad Sci U S A. Jan. 1, 1992;89(1):392-6.

Walsh, et al. Detection of inherited mutations for breast and ovarian cancer using genomic capture and massively parallel sequencing. Proc Natl Acad Sci U S A. Jul. 13, 2010; 107(28):12629-33. doi: 10.1073/pnas.1007983107. Epub Jun. 28, 2010.

Wang, J. et al. "CREST Maps Somatic Structural Variation in Cancer Genomes with Base-Pair Resolution" Nature Methods (Jun. 12, 2011) 8(8):652-654.

Weber, et al. A real-time polymerase chain reaction assay for quantification of allele ratios and correction of amplification bias. Anal Biochem. Sep. 15, 2003;320(2):252-8.

Willing, E.M. et al. "Paired-end RAD-seq for de novo assembly and marker sign without available reference" Bioinformatics (2011) 27(16):2187-2193.

Wojdacs, et al. Primer design versus PCR bias in methylation independent PCR amplifications. Epigenetics. May 16, 2009;4(4):231-4. Epub May 14, 2009.

Wood, et al. Using next-generation sequencing for high resolution multiplex analysis of copy number variation from nanogram quantities of DNA from formalin-fixed paraffin-embedded specimens. Nucleic Acids Res. Aug. 2010;38(14): e151. doi: 10.1093/nar/gkq510. Epub Jun. 4, 2010.

Wu, T-L. et al. "Cell-free DNA: measurement in various carcinomas and establishment of normal reference range" Clin Chim Acta (2002) 321:77-87.

Xu, et al. "FastUniq: A Fast De Novo Duplicates Removal Tool for Paired Short Reads" PLOS One (2012) 7(12): e52249 pp. 1-6.

Yandell, et al. A probabilistic disease-gene finder for personal genomes. Genome Res. Sep. 2011;21(9):1529-42. doi: 10.1101/gr.123158.111. Epub Jun. 23, 2011.

Yoon, et al. Sensitive and accurate detection of copy number variants using read depth of coverage. Genome Res. Sep. 2009; 19(9):1586-92. doi: 10.1101/gr.092981.109. Epub Aug. 5, 2009.

Zhang, et al. The impact of next-generation sequencing on genomics. J Genet Genomics. Mar. 2, 20110;38(3):95-109. doi: 10.1016/j.jgg.2011.02.003. Epub Mar. 15, 2011.

Zill, O.A. et al. "The Landscape of Actionable Genomic Alterations in Cell-Free Circulating Tumor DNA from 21,807 Advanced Cancer Patients" Clin Canc Res (2018) 24(15):3528-3538.

* cited by examiner

Deletion
Variant

301

Deleted

Variant
Sequence

L1                                    L2

Deletion Variant
Expected
Alignment

302

Reference
Sequence 316          317

L1                                    L2

302A
304A 302B
304B

Insertion
Variant

303   Inserted

Variant
Sequence

L1                                    L2

Insertion Variant
Expected
Alignment

Reference
Sequence 316   (317?)

L1                                    L2

302A          302B
304A          304B

Rearrangement Variant
Expected Alignment                316

L1

302A          302B
304A          304B

L2

317

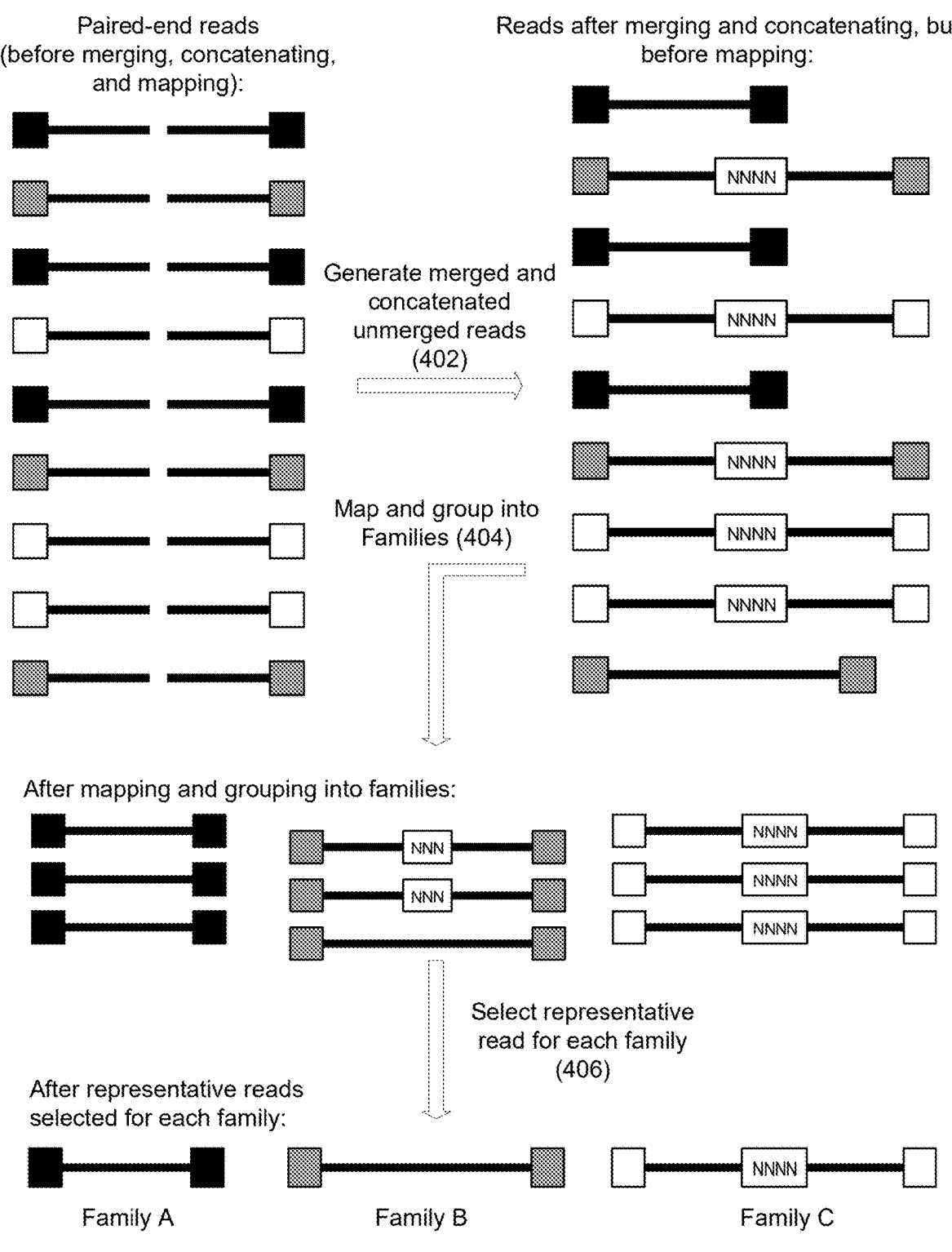

Paired-end reads
(before merging, concatenating,
and mapping):

Reads after merging and concatenating, but
before mapping:

Generate merged and
concatenated
unmerged reads
(402)

Map and group into
Families (404)

After mapping and grouping into families:

Select representative
read for each family
(406)

After representative reads
selected for each family:

Family A                    Family B                    Family C

FIG. 4

GENETIC VARIANT DETECTION BASED ON MERGED AND UNMERGED READS

CROSS-REFERENCE TO RELATED APPLICATIONS

This application is a continuation of U.S. patent application Ser. No. 16/559,465, filed Sep. 3, 2019, which claims the benefit of U.S. provisional patent application No. 62/726,131, filed Aug. 31, 2018, both of which are fully incorporated by reference herein for all purposes.

BACKGROUND

Genetic variants, such as insertions, deletions, substitutions, rearrangements and copy number variants may be correlated with diseases. Genetic variants such as insertions and deletions represent the second most frequent class of genetic variants in a human genome, after single nucleotide polymorphisms. The insertions and/or deletions also contribute to pathogenesis of diseases, gene expression and functionality. Next-generation sequencing technologies or high-throughput sequencing can be employed to detect genetic variants. Identifying genetic variants accurately is critical for using the next-generation sequencing technologies in identifying the genetic variants associated with diseases.

SUMMARY

The disclosure relates to computer technology that provides precision diagnosis based on a determination of various states of nucleic acids such as a DNA or RNA from a genome, chromosome, or other genetic portion sequenced from a sample. The state may include a variation from a wildtype sequence of the nucleic acid sequenced from the sample. Such variation may include, without limitation, an insertion, a deletion, a rearrangement, a copy number variant (which may include a series of insertions or deletions relative to the wildtype state), and/or other states. A rearrangement may include a portion of a sequence (such as a genomic sequence) that is moved or copied to a location of the sequence that otherwise does not include the portion in a wildtype or reference state. The precision diagnostic may be based on an analysis of sequence reads generated from the sample. To reduce instances of laboratory-induce variants, the precision diagnostic may be further based on a modification of laboratory system processing that may reduce the occurrence of laboratory-induce variants.

The system may be used to not only for precision diagnosis but also precision verification of gene therapies, such to confirm an intentional introduction of a variant for therapeutic purposes. In one aspect, the disclosure relates to methods and computer systems improved to detect nucleic acid variants in a sample of a subject.

For example, in some embodiments, a method for detecting nucleic acid variants in a sample of nucleic acid molecules from a subject may include accessing a plurality of paired-end reads generated from the sample of nucleic acid molecules from the subject. The method may further include identifying a plurality of pairs of paired-end reads from among the plurality of paired-end reads based on an overlap criterion, and generating a plurality of merged reads based on the plurality of pairs of overlapping paired-end reads. A merged read may include a sequence based on respective sequences of a pair of overlapping paired-end reads. The method may include identifying a plurality of unmerged reads from among the plurality of paired-end reads. A given unmerged read may include a paired-end read that does not satisfy an overlap criterion with a mated (or corresponding) paired-end read. The method may further include aligning the plurality of merged reads and the plurality of unmerged reads to a reference genome to generate a plurality of aligned reads, and identifying a plurality of split reads from among the plurality of aligned reads. A given split read includes a first subsequence portion that aligns to a first nucleic acid locus of the reference sequence and a second subsequence portion that aligns to a second nucleic acid locus of the reference sequence. The method may further include determining, for a given split read, a breakpoint comprising a pair of genomic locations corresponding to the first nucleic acid locus and the second nucleic acid locus, clustering the plurality of split reads based on respective breakpoints of the plurality of split reads to generate a plurality of variant clusters, and identifying any one or more of the plurality of variant clusters that meet a predetermined criterion as indicative of a detected variant.

In some embodiments, a given unmerged read of the plurality of unmerged reads has a corresponding unmerged read. In these embodiments, the method may further include generating, for a given unmerged read and corresponding unmerged read, an artificial nucleotide sequence. The method may further include concatenating the artificial nucleotide sequence to a first sequence of the unmerged read and a second sequence of the corresponding unmerged read and a sequence of the corresponding unmerged read.

In some embodiments, the artificial nucleotide sequence is located between the first and second sequences. In some embodiments, the artificial nucleotide sequence is at least 1 nucleotide, at least 2 nucleotides, at least 5 nucleotides, at least 10 nucleotides, at least 15 nucleotides, at least 20 nucleotides, at least 30 nucleotides, at least 40 nucleotides, at least 50 nucleotides, or at least 100 nucleotides in length. In some embodiments, a location of a breakpoint is approximated to be located within the artificial nucleotide sequence. In some embodiments, a group comprises split reads having breakpoints within the artificial nucleotide sequence and split reads having breakpoints within the first or second subsequence portions.

In some of these embodiments, the breakpoints are no more than 5 nucleotides, no more than 10 nucleotides or no more than 25 nucleotides apart.

In some embodiments, the predetermined criterion comprises having more than one split read in a group. In some embodiments, the predetermined criterion may include: having at least one split read within a group in which a breakpoint occurs within the first or the second subsequence.

In some embodiments, the sample is a bodily fluid sample selected from the group consisting of blood, plasma, serum, urine, saliva, mucosal excretions, sputum, stool, and tears. In some embodiments, the subject has a disease, which may include cancer.

In some embodiments, the nucleic acid molecules are DNA, which may include cell-free DNA. In some embodiments, the method may include generating copies of the cell-free DNA molecules prior to sequencing.

In some embodiments, the method may include attaching one or more adapters comprising barcodes to the nucleic acid molecules prior to sequencing. In some embodiments, the adapters are randomly attached to both ends of the nucleic acid molecules.

In some embodiments, the nucleic acid molecules are uniquely barcoded.

In some embodiments, the nucleic acid molecules are non-uniquely barcoded.

In some embodiments, each barcode comprises a fixed, semi-random, random oligonucleotide sequence that in combination with a diversity of molecules sequenced from a selected region enables identification of unique molecules.

In some embodiments, the method may include selectively enriching the nucleic acid molecules for a plurality of nucleic acid loci prior to sequencing.

In some embodiments, the method may include amplifying polynucleotides from the sample of the subject.

In some embodiments, the method may include determining that the detected variant comprises an insertion, a deletion, or a nucleic acid rearrangement.

In some embodiments, the method may include determining a predicted disease state based on the detected variant.

In some embodiments, a method for detecting nucleic acid variants in a sample of nucleic acid molecules from a subject may include accessing a plurality of paired-end reads generated from the sample of nucleic acid molecules from the subject, generating a plurality of merged reads based on respective mated pairs of paired-end reads that satisfy an overlap criterion, and identifying a plurality of unmerged reads from among the plurality of paired-end reads. A given unmerged read comprises a paired-end read that does not satisfy an overlap criterion with a corresponding mated paired-end read. The method may further include generating a plurality of concatenated unmerged reads based on the plurality of unmerged reads, aligning, by the computer system, the plurality of merged reads and the plurality of concatenated unmerged reads to a reference genome to generate a plurality of aligned reads, and identifying, by the computer system, a plurality of split reads from among the plurality of aligned reads. A given split read from among the plurality of split reads includes a first subsequence portion that aligns to a first nucleic acid locus of the reference sequence and a second subsequence portion that aligns to a second nucleic acid locus of the reference sequence, the second nucleic acid locus different from the first nucleic acid locus. The method may further include identifying one or more variants based on the plurality of split reads.

In some embodiments, the method may further include identifying a plurality of merged split reads from among the plurality of split reads that originated from the plurality of merged reads, generating a plurality of variant clusters based on the plurality of merged split reads, and identifying pairs of breakpoints for a given one of the plurality of variant clusters. A given pair of breakpoints comprises a first breakpoint corresponding to a corresponding first nucleic acid locus and a second breakpoint corresponding to a corresponding second nucleic acid locus. One or more variants are identified based on corresponding ones of the identified pairs of breakpoints.

In some embodiments, the method may further include identifying one or more of the plurality of variant clusters that meet a criterion as the one or more variants.

In some embodiments, the method may further include identifying a plurality of unmerged split reads from among the plurality of split reads that originated from the plurality of unmerged reads, and determining that an unmerged split read aligns to the first nucleic acid locus and the second nucleic acid locus. The alignment of the unmerged split read to the first nucleic acid locus and the second nucleic acid locus is used as the criterion.

In some embodiments, the predetermined criterion comprises having more than one split read in a group. In some embodiments, the predetermined criterion comprises having at least one split read within a group in which a breakpoint occurs within the first or the second subsequence.

In some embodiments, generating the plurality of variant clusters is based further on one or more of the plurality of concatenated unmerged reads flanking a merged read.

In some embodiments, the method may further include identifying a plurality of unmerged split reads from among the plurality of split reads that originated from the plurality of unmerged reads, generating a plurality of variant clusters based on the plurality of unmerged split reads, and identifying pairs of breakpoints for a given one of the plurality of variant clusters, wherein a given pair of breakpoints comprises a first breakpoint corresponding to a corresponding first nucleic acid locus and a second breakpoint corresponding to a corresponding second nucleic acid locus. The one or more variants are identified based on corresponding ones of the identified pairs of breakpoints.

In some embodiments, the method may further include generating a plurality of variant clusters based on the plurality of split reads, and identifying pairs of breakpoints for a given one of the plurality of variant clusters, wherein a given pair of breakpoints comprises a first breakpoint corresponding to a corresponding first nucleic acid locus and a second breakpoint corresponding to a corresponding second nucleic acid locus. The one or more variants are identified based on corresponding ones of the identified pairs of breakpoints.

In some embodiments, the method may further include determining that the one or more variants comprise an insertion, a deletion, or a nucleic acid rearrangement.

In some embodiments, the method may further include determining a predicted disease state based on the detected one or more variants.

In some embodiments, a system for detecting nucleic acid variants in a sample of nucleic acid molecules from a subject may include a computer system. The computer system may include a processor programmed to access a plurality of paired-end reads generated from the sample of nucleic acid molecules from the subject, identify a plurality of pairs of paired-end reads from among the plurality of paired-end reads based on an overlap criterion, and generate a plurality of merged reads based on the plurality of pairs of overlapping paired-end reads. A merged read may include a sequence based on respective sequences of a pair of overlapping paired-end reads. The processor may be further programmed to identify a plurality of unmerged reads from among the plurality of paired-end reads. A given unmerged read may include a paired-end read that does not satisfy an overlap criterion with a mated paired-end read. The processor may be further programmed to align the plurality of merged reads and the plurality of unmerged reads to a reference genome to generate a plurality of aligned reads, identify a plurality of split reads from among the plurality of aligned reads, wherein a given split read includes a first subsequence portion that aligns to a first nucleic acid locus of the reference sequence and a second subsequence portion that aligns to a second nucleic acid locus of the reference sequence, determine, for a given split read, a breakpoint comprising a pair of genomic locations corresponding to the first nucleic acid locus and the second nucleic acid locus, cluster the plurality of split reads based on respective breakpoints of the plurality of split reads to generate a plurality of variant clusters, and identify any one or more of the plurality of variant clusters that meet a predetermined criterion as a detected variant.

In some embodiments, a given unmerged read of the plurality of unmerged reads has a corresponding unmerged read. In these embodiments, the processor may be further programmed to generate, for a given unmerged read and corresponding unmerged read, an artificial nucleotide sequence.

In some embodiments, the processor may be further programmed to concatenate the artificial nucleotide sequence to a first sequence of the unmerged read and a second sequence of the corresponding unmerged read and a sequence of the corresponding unmerged read.

In some embodiments, a location of a breakpoint is approximated to be located within the artificial nucleotide sequence.

In some embodiments, a group comprises split reads having breakpoints within the artificial nucleotide sequence and split reads having breakpoints within the first or second subsequence portions.

In some embodiments, the system may further include a laboratory system to amplify polynucleotides from the sample of the subject.

In some embodiments, the processor may be further programmed to determine that the detected variant comprises an insertion, a deletion, or a nucleic acid rearrangement.

In some embodiments, the processor may be further programmed to determine a predicted disease state based on the detected variant.

In some embodiments, a system for detecting nucleic acid variants in a sample of nucleic acid molecules from a subject may include a computer system. The computer system may include a processor programmed to access a plurality of paired-end reads generated from the sample of nucleic acid molecules from the subject, generate a plurality of merged reads based on respective mated pairs of paired-end reads that satisfy an overlap criterion, and identify a plurality of unmerged reads from among the plurality of paired-end reads. A given unmerged read comprises a paired-end read that does not satisfy an overlap criterion with a corresponding mated paired-end read. The processor may be further programmed to generate a plurality of concatenated unmerged reads based on the plurality of unmerged reads, align the plurality of merged reads and the plurality of concatenated unmerged reads to a reference genome to generate a plurality of aligned reads, identify a plurality of split reads from among the plurality of aligned reads, wherein a given split read from among the plurality of split reads includes a first subsequence portion that aligns to a first nucleic acid locus of the reference sequence and a second subsequence portion that aligns to a second nucleic acid locus of the reference sequence, and identify one or more variants based on the plurality of split reads.

In some embodiments, the system may further include a laboratory system to amplify polynucleotides from the sample of the subject.

In some embodiments, the processor may be further programmed to determine that the one or more variant comprises an insertion, a deletion, or a nucleic acid rearrangement.

In some embodiments, the processor may be further programmed to determine a predicted disease state based on the one or more variants.

In some embodiments, the results of the systems and/or methods disclosed herein are used as an input to generate a report. The report may be in a paper or electronic format. For example, information on, and/or information derived from, the presence or absence of variants in a sample, as determined by the methods or systems disclosed herein, can be displayed in such a report. The methods or systems disclosed herein may further comprise a step of communicating the report to a third party, such as the subject from whom the sample derived or a health care practitioner.

The various steps of the methods disclosed herein, or the steps carried out by the systems disclosed herein, may be carried out at the same time or different times, and/or in the same geographical location or different geographical locations, e.g. countries. The various steps of the methods disclosed herein can be performed by the same person or different people.

BRIEF DESCRIPTION OF THE FIGURES

FIG. 4 illustrates an example schematic data flow for generating representative reads, according to an embodiment of the disclosure.

DEFINITIONS

Figure 1:
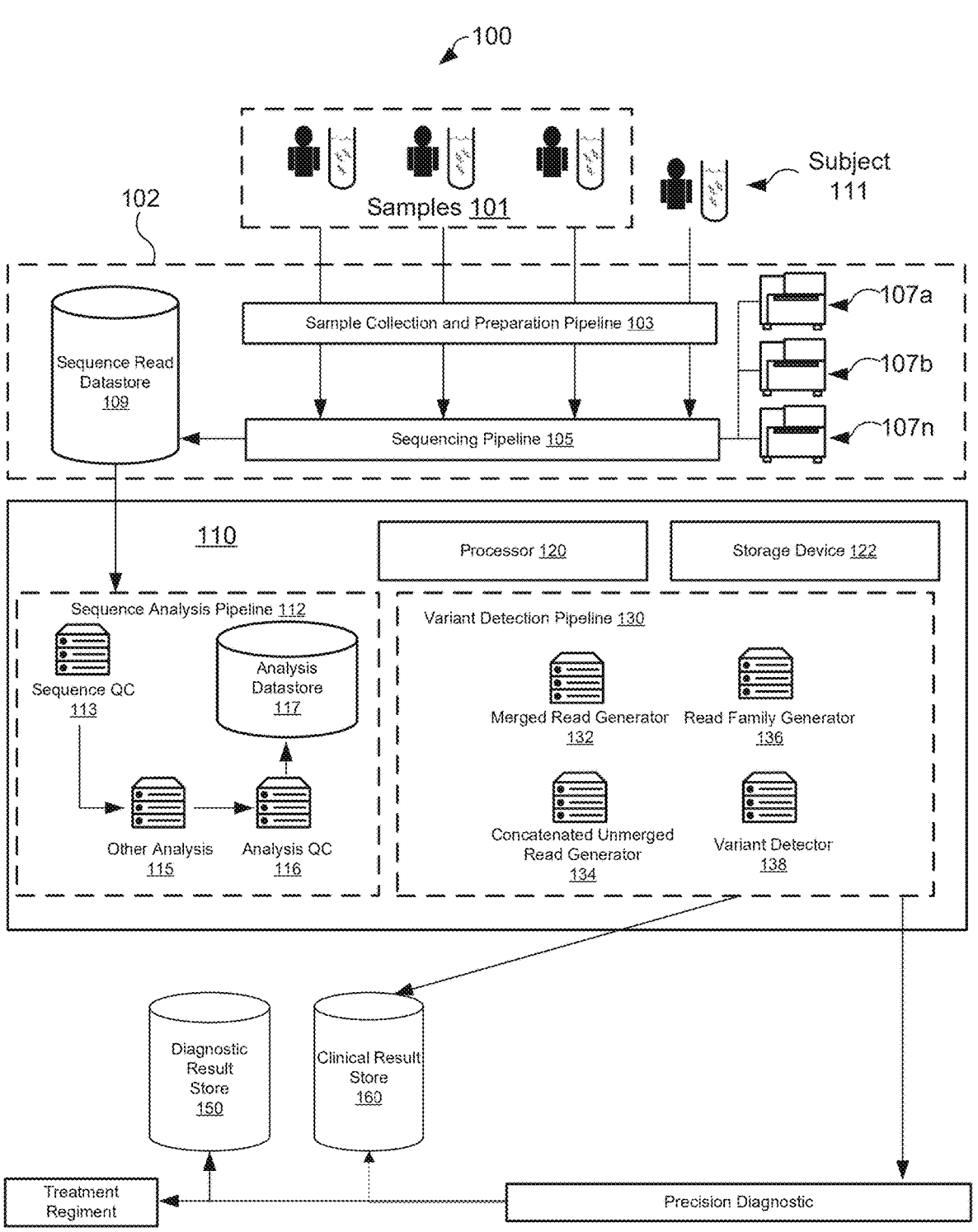
FIG. 1 illustrates an example of a system for identifying nucleic acid variants in a sample of a subject, according to an embodiment of the disclosure.

In order for the present disclosure to be more readily understood, certain terms are first defined below. Additional definitions for the following terms and other terms may be set forth through the specification. If a definition of a term set forth below is inconsistent with a definition in an application or patent that is incorporated by reference, the definition set forth in this application should be used to understand the meaning of the term.

As used in this specification and the appended claims, the singular forms "a," "an," and "the" include plural references unless the context clearly dictates otherwise. Thus, for example, a reference to "a method" includes one or more methods, and/or steps of the type described herein and/or which will become apparent to those persons of ordinary skill in the art upon reading this disclosure and so forth.

It is also to be understood that the terminology used herein is for the purpose of describing particular embodiments only, and is not intended to be limiting. Further, unless defined otherwise, all technical and scientific terms used herein have the same meaning as commonly understood by one of ordinary skill in the art to which this disclosure pertains. In describing and claiming the methods, computer readable media, and systems, the following terminology, and grammatical variants thereof, will be used in accordance with the definitions set forth below.

Adapter: As used herein, "adapter" refers to a short nucleic acid (e.g., less than about 500 nucleotides, less than about 100 nucleotides, or less than about 50 nucleotides in length) that is typically at least partially double-stranded and used to link to either or both ends of a given sample nucleic acid molecule. Adapters can include nucleic acid primer binding sites to permit amplification of a nucleic acid molecule flanked by adapters at both ends, and/or a sequencing primer binding site, including primer binding sites for sequencing applications, such as various next-generation sequencing (NGS) applications. Adapters can also include binding sites for capture probes, such as an oligonucleotide attached to a flow cell support or the like. Adapters can also include a nucleic acid tag as described herein. Nucleic acid tags are typically positioned relative to amplification primer and sequencing primer binding sites, such that a nucleic acid tag is included in amplicons and sequence reads of a given nucleic acid molecule. The same or different adapters can be linked to the respective ends of a nucleic acid molecule. In some embodiments, the adapter of the same sequence is linked to the respective ends of the nucleic acid molecule except that the nucleic acid tag differs. In some embodiments, the adapter is a Y-shaped adapter in which one end is blunt ended or tailed as described herein, for joining to a nucleic acid molecule, which is also blunt ended or tailed with one or more complementary nucleotides. In still other example embodiments, an adapter is a bell-shaped adapter that includes a blunt or tailed end for joining to a nucleic acid molecule to be analyzed. Other examples of adapters include T-tailed and C-tailed adapters.

Barcode: As used herein, "barcode" or "molecular barcode" in the context of nucleic acids refers to a nucleic acid molecule comprising a sequence that can serve as a molecular identifier. For example, individual "barcode" sequences are typically added to each DNA fragment during next-generation sequencing (NGS) library preparation so that each sequencing read can be identified and sorted before the final data analysis.

Deoxyribonucleic Acid or Ribonucleic Acid: As used herein, "deoxyribonucleic acid" or "DNA" refers to a natural or modified nucleotide which has a hydrogen group at the 2'-position of the sugar moiety. DNA typically includes a chain of nucleotides comprising four types of nucleotide bases; adenine (A), thymine (T), cytosine (C), and guanine (G). As used herein, "ribonucleic acid" or "RNA" refers to a natural or modified nucleotide which has a hydroxyl group at the 2'-position of the sugar moiety. RNA typically includes a chain of nucleotides comprising four types of nucleotide bases A, uracil (U), G, and C. As used herein, the term "nucleotide" refers to a natural nucleotide or a modified nucleotide. Certain pairs of nucleotides specifically bind to one another in a complementary fashion (called complementary base pairing). In DNA, adenine (A) pairs with thymine (T) and cytosine (C) pairs with guanine (G). In RNA, adenine (A) pairs with uracil (U) and cytosine (C)

pairs with guanine (G). When a first nucleic acid strand binds to a second nucleic acid strand made up of nucleotides that are complementary to those in the first strand, the two strands bind to form a double strand. As used herein, "nucleic acid sequencing data," "nucleic acid sequencing information," "sequence information," "nucleic acid sequence," "nucleotide sequence", "genomic sequence," "genetic sequence," or "fragment sequence," or "nucleic acid sequencing read" denotes any information or data that is indicative of the order and identity of the nucleotide bases (e.g., adenine, guanine, cytosine, and thymine or uracil) in a molecule (e.g., a whole genome, whole transcriptome, exome, oligonucleotide, polynucleotide, or fragment) of a nucleic acid such as DNA or RNA. It should be understood that the present teachings contemplate sequence information obtained using all available varieties of techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, and electronic signature-based systems.

Designated Position: The term "designated position" in a reference sequence refers to a genomic coordinate in the reference sequence.

Family of Reads: The phrase "family of reads' refers to a grouping of an unpaired read, a merged read, an unmerged read, a concatenated unmerged read, and/or other read that are grouped together based on alignment to a reference sequence, inclusion of a molecular barcode, and/or other grouping criterion.

Genetic Variant: A genetic variant refers to an alteration, variant or polymorphism in a nucleic acid sample or genome of a subject. Such alteration, variant or polymorphism can be with respect to a reference genome, which may be a reference genome of the species (e.g., for human, hG19 or hG38), the subject or other individual. Variations include one or more single nucleotide variations (SNVs), insertions, deletions, repeats, small insertions, small deletions, small repeats, structural variant junctions, variable length tandem repeats, and/or flanking sequences, copy number variants (CNVs), transversions, gene fusions and other rearrangements are also forms of genetic variation. A variation can be a single nucleotide variation (SNV), insertion or deletion (indel), repeat, copy number variation (CNV), transversion, or a combination thereof.

Merged Read: A "merged read" refers to a sequence generated by joining together respective sequences of paired-end reads of a mated pair when an alignment between the respective sequences satisfies the overlap criterion.

Nucleic Acid Tag: As used herein, "nucleic acid tag" refers to a short nucleic acid (e.g., less than about 500 nucleotides, about 100 nucleotides, about 50 nucleotides, or about 10 nucleotides in length), used to distinguish nucleic acids from different samples (e.g., representing a sample index), or different nucleic acid molecules in the same sample (e.g., representing a molecular barcode), of different types, or which have undergone different processing. The nucleic acid tag comprises a predetermined, fixed, non-random, random or semi-random oligonucleotide sequence. Such nucleic acid tags may be used to label different nucleic acid molecules or different nucleic acid samples or subsamples. Nucleic acid tags can be single-stranded, double-stranded, or at least partially double-stranded. Nucleic acid tags optionally have the same length or varied lengths. Nucleic acid tags can also include double-stranded molecules having one or more blunt-ends, include 5' or 3' single-stranded regions (e.g., an overhang), and/or include one or more other single-stranded regions at other locations within a given molecule. Nucleic acid tags can be attached to one end or to both ends of the other nucleic acids (e.g., sample nucleic acids to be amplified and/or sequenced). Nucleic acid tags can be decoded to reveal information such as the sample of origin, form, or processing of a given nucleic acid. For example, nucleic acid tags can also be used to enable pooling and/or parallel processing of multiple samples comprising nucleic acids bearing different molecular barcodes and/or sample indexes in which the nucleic acids are subsequently being deconvolved by detecting (e.g., reading) the nucleic acid tags. Nucleic acid tags can also be referred to as identifiers (e.g. molecular identifier, sample identifier). Additionally, or alternatively, nucleic acid tags can be used as molecular barcodes (e.g., to distinguish between different molecules or amplicons of different parent molecules in the same sample or sub-sample). This includes, for example, uniquely tagging different nucleic acid molecules in a given sample, or non-uniquely tagging such molecules. In the case of non-unique tagging applications, a limited number of tags (i.e., molecular barcodes) may be used to tag nucleic acid molecules such that different molecules can be distinguished based on their endogenous sequence information (for example, start and/or stop positions where they map to a selected reference genome, a subsequence of one or both ends of a sequence, and/or length of a sequence) in combination with at least one molecular barcode. Typically, a sufficient number of different molecular barcodes are used such that there is a low probability (e.g., less than about a 10%, less than about a 5%, less than about a 1%, or less than about a 0.1% chance) that any two molecules may have the same endogenous sequence information (e.g., start and/or stop positions, subsequences of one or both ends of a sequence, and/or lengths) and also have the same molecular barcode.

Overlap Criterion: An "overlap criterion" may refer to an alignment quality sufficient to determine aligned portions of two paired-end reads represent the same underlying sequence. The overlap criterion may include, without limitation, a minimum overlap of at least about 1 base, least about 2 bases, least about 3 bases, least about 4 bases, least about 5 bases, least about 10 bases, least about 15 bases, least about 20 bases, least about 25 bases, least about 30 bases, least about 35 bases, least about 40 bases, least about 45 bases, least about 50 bases, least about 55 bases, least about 60 bases, least about 65 bases, least about 70 bases, least about 75 bases, least about 80 bases, least about 85 bases, least about 90 bases, least about 95 bases, or least about 100 bases. Alternatively, or additionally, an overlap criterion may include, without limitation, a minimum alignment identity of at least about 5%, least about 10%, least about 15%, least about 20%, least about 25%, least about 30%, least about 35%, least about 40%, least about 45%, least about 50%, least about 55%, least about 60%, least about 65%, least about 70%, least about 75%, least about 80%, least about 85%, least about 90%, least about 95%, or more. In some cases, a criterion may require at least a 15 base-pair overlap with at least about 90% identity between the strands. In other cases, the overlap criterion may require at a least 19 base-pair overlap with at least 90% identity between the strands. The overlapping region is represented by a strong peak when using sliding window analysis. For example, the overlapping region is slid to include a base on each end of the overlapping region and identity between the strands is computed until both strands completely overlap each other. The identity between the strands is computed as percentage of identity. The percentage of identity is directly proportional to the height of the peak. The merged reads or the paired-end reads with a single strong peak are selected for further analysis.

Paired-End Read: A "paired-end read" refers to a sequence read generated from a paired-end sequencing strategy in which both strands or sense of a nucleic acid amplicon or molecule is sequenced to generate a pair of paired-end reads. A pair of paired-end reads refers to two paired-end reads sequenced from respective strands or sense of the same nucleic acid amplicon or molecule. A pair of paired-end reads will also be referred to interchangeably herein as a "mated pair."

Polynucleotide: A "polynucleotide", "nucleic acid", "nucleic acid molecule", or "oligonucleotide" refers to a linear polymer of nucleosides (including deoxyribonucleosides, ribonucleosides, or analogs thereof) joined by internucleosidic linkages. Typically, a polynucleotide comprises at least three nucleosides. Oligonucleotides often range in size from a few monomeric units, e.g. 3-4, to hundreds of monomeric units. Whenever a polynucleotide is represented by a sequence of letters, such as "ATGCCTG," it will be understood that the nucleotides are in $5'{\to}3'$ order from left to right and that "A" denotes deoxyadenosine, "C" denotes deoxycytidine, "G" denotes deoxyguanosine, and "T" denotes thymidine, unless otherwise noted. The letters A, C, G, and T may be used to refer to the bases themselves, to nucleosides, or to nucleotides comprising the bases, as is standard in the art. A nucleic acid molecule can be conceptually divided into a 5' terminal end, an internal portion and a 3' terminal end. Terminal ends can be designated based a predetermined number of nucleotides from the terminus. For example, 5' terminal end be represented by, e.g., the 20 terminal nucleotides to 5' end. The 3' terminal end be represented by, e.g., the 20 terminal nucleotides to the 3' end. Alternatively, the nucleic acid molecule can be divided into a terminal portion, as described, and a remainder.

Processing: The terms "processing", "calculating", and "comparing" can be used interchangeably. The term can refer to determining a difference, e.g., a difference in number or sequence. For example, gene expression, copy number variation (CNV), indel, and/or single nucleotide variant (SNV) values or sequences can be processed.

Reference Sequence: A reference sequence is a known sequence used for purposes of comparison with experimentally determined sequences. For example, a known sequence can be an entire genome, a chromosome, or any segment thereof. A reference typically includes at least 20, 50, 100, 200, 250, 300, 350, 400, 450, 500, 1,000, 10,000, 50,000, 100,000, 1,000,000, 5,000,000 or more nucleotides. A reference sequence can align with a single contiguous sequence of a genome or chromosome or can include non-contiguous segments aligning with different regions of a genome or chromosome. Reference human genomes include, e.g., hG19 and hG38.

Representative Read: The term "representative read" refers to a sequence that represents a family of reads that were grouped together. The sequence of the representative read may be determined based on a representative single one of the reads in the family or via consensus of two or more reads in the family.

Sequence Information: As used herein, "sequence information" in the context of a nucleic acid polymer means the order and identity of monomer units (e.g., nucleotides, etc.) in that polymer.

Sequencing: As used herein, the term "sequencing" refers to any of a number of technologies used to determine the sequence of a biomolecule, e.g., a nucleic acid such as DNA or RNA. Exemplary sequencing methods include, but are not limited to, targeted sequencing, single molecule real-time sequencing, exon sequencing, electron microscopy-based sequencing, panel sequencing, transistor-mediated sequencing, direct sequencing, random shotgun sequencing, Sanger dideoxy termination sequencing, whole-genome sequencing, sequencing by hybridization, pyrosequencing, capillary electrophoresis, duplex sequencing, cycle sequencing, single-base extension sequencing, solid-phase sequencing, high-throughput sequencing, massively parallel signature sequencing, emulsion PCR, co-amplification at lower denaturation temperature-PCR (COLD-PCR), multiplex PCR, sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLID™ sequencing, MS-PET sequencing, and a combination thereof. In some embodiments, sequencing can be performed by a gene analyzer such as, for example, gene analyzers commercially available from Illumina or Applied Biosystems. The phrase "next generation sequencing" or NGS refers to sequencing technologies having increased throughput as compared to traditional Sanger- and capillary electrophoresis-based approaches, for example, with the ability to generate hundreds of thousands of relatively small sequence reads at a time. Some examples of next generation sequencing techniques include, but are not limited to, sequencing by synthesis, sequencing by ligation, and sequencing by hybridization.

Sequencing Run: The phrase "sequencing run" refers to any step or portion of a sequencing experiment performed to determine some information relating to at least one biomolecule (e.g., a nucleic acid molecule such as DNA or RNA).

Split Read: A "split read" refers to a sequence read in which different subsequence portions of a sequence of the sequence read align to different loci of a reference sequence to which the split read is aligned, indicating that a variant may have been sequenced relative to the reference sequence. A split read may be an unpaired read, a merged read, an unmerged read, a concatenated unmerged read, and/or a representative read.

Subject: As used herein, a "subject" refers to an animal, such as a mammalian species (preferably human) or avian (e.g., bird) species, or other organism. More specifically, a subject can be a vertebrate, e.g., a mammal such as a mouse, a primate, a simian or a human. Animals include farm animals, sport animals, and pets. A subject can be a healthy individual, an individual that has symptoms or signs or is suspected of having a disease (e.g., cancer) or a predisposition to the disease, or an individual that is in need of therapy or suspected of needing therapy.

Unmerged Read: An unmerged read refers to a paired-end read of a mated pair in which an alignment with the corresponding paired-end read of the mated pair (which itself is an unmerged read) does not satisfy the overlap criterion. A concatenated unmerged read refers to a sequence generated by concatenating the respective sequences of a mated pair of unmerged reads, joined together by an artificial sequence composed of one or more placeholders.

DETAILED DESCRIPTION

FIG. 1 illustrates an example of a system 100 for identifying nucleic acid variants in a sample of subject 111, according to an embodiment of the disclosure. The system 100 may process one or more samples 101 from the subject 111 to generate sequence reads for variant detection. The system 100 may include a laboratory system 102, a computer system 110, and/or other components. It should be noted that the laboratory system 102 and the computer system 110 may be remote from one another, and connected to one another through a computer network (not illustrated). The laboratory system 102 may include a sample collection and preparation pipeline 103, a sequencing pipeline 105, a sequence read datastore 109, and/or other components. The sequencing pipeline 105 may include one or more sequencing devices 107 (illustrated in FIG. 1 as sequencing devices 107a . . . n).

The computer system 110 may include a sequence analysis pipeline 112, a processor 120, a storage device 122, a variant detection pipeline 130, and/or other components.

The sequence analysis pipeline 112 may include a sequence quality control (QC) component 113, other analysis components 115, and an analysis QC component 116. Output from the sequence analysis pipeline 112 may be stored in an analysis datastore 117.

Generally speaking, the processor 120 may implement (be programmed by) various components of the variant detection pipeline 130, such as a merged read generator 132, an concatenated unmerged read generator 134, a read family generator 136, a variant detector 138, and/or other components. Alternatively, it should be noted that each of these components of the variant detection pipeline 130 may include a hardware module. Although illustrated separately for convenience, one or more of the various components or instructions, such as the merged read generator 132, concatenated unmerged read generator 134, read family generator 136, and/or variant detector 138 may be integrated with one another. In any event, the variant detection pipeline 130 may cause the computer system 110 to identify variants, diseases from the variants (precision diagnostics), and/or treatment regiments. The precision diagnostic and treatment regimen may be stored in a repository such as clinical result store 160 or diagnostic result store 150.

Figure 2A:
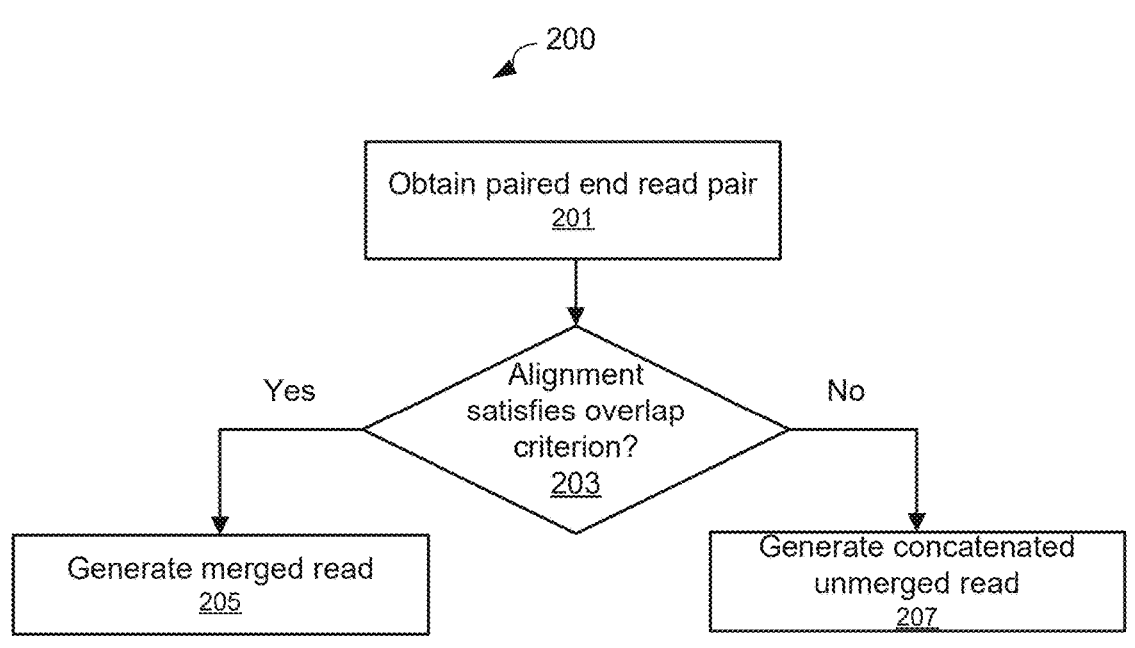
FIG. 2A illustrates a method of generating merged reads or concatenated unmerged reads from paired-end read pairs based on an overlap criterion, according to an embodiment of the disclosure.

FIG. 2A illustrates a method 200 of generating merged reads or concatenated unmerged reads from paired-end read pairs based on an overlap criterion, according to an embodiment of the disclosure. At 201, the method 200 may include obtaining a paired end read pair. For example, the method 200 may access the paired-end read pair from the sequence read datastore 109 or the analysis datastore 117. At 203, the method 200 may include determining whether an alignment between each of the paired-end reads of the pair satisfy an overlap criterion. If yes, at 205, the method 200 may include generating a merged read. If not, at 207, the method 200 may include generating a concatenated unmerged read.

Figure 2B:
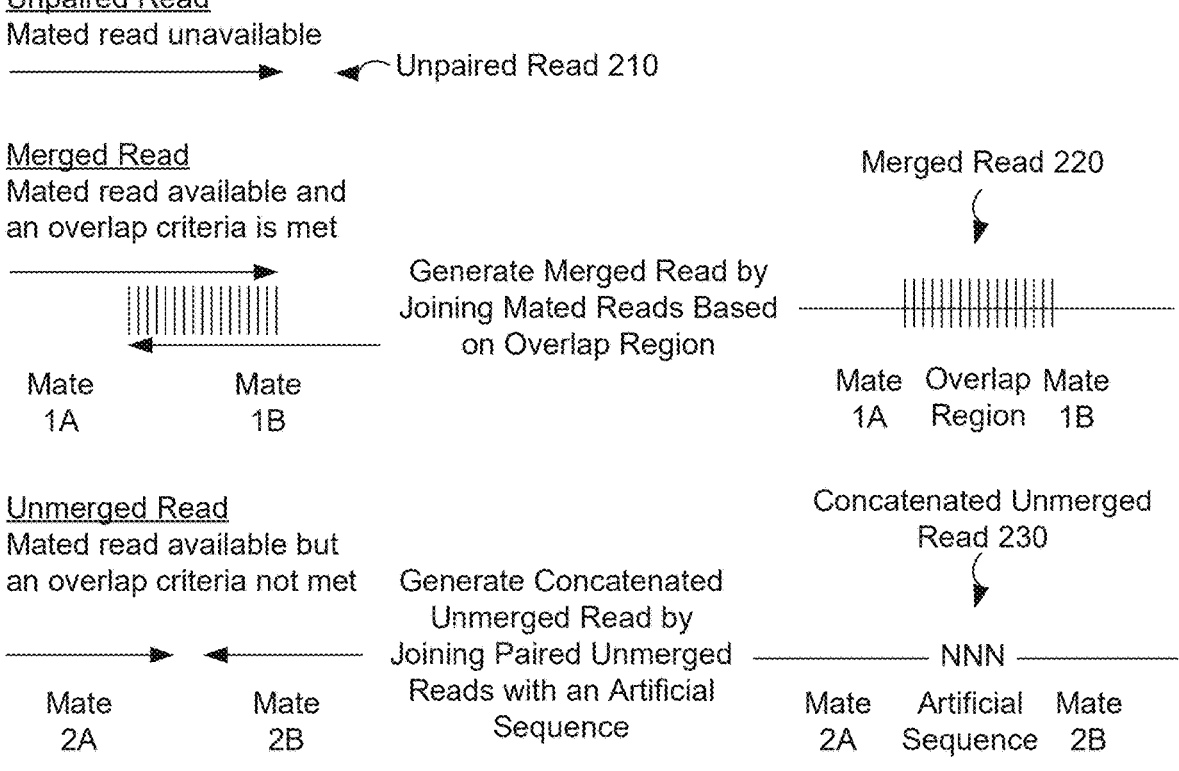
FIG. 2B illustrates types of sequence reads used to identify nucleic acid variants, according to an embodiment of the disclosure.

Merged reads and concatenated unmerged reads are described further with reference to FIG. 2B, which illustrates types of sequence reads used by the system 100 to identify nucleic acid variants, according to an embodiment of the disclosure. For example, the computer system 110 may use and/or generate sequence reads that include unpaired reads 210, merged reads 220, unmerged reads, and concatenated unmerged reads 230 to identify nucleic acid variants and corresponding precision diagnosis and/or treatment.

An unpaired read 210 may include a sequence read in which a corresponding paired-end read is unavailable. In some examples that do not use paired-end sequencing, an unpaired read may result from the lack of paired-end reads. In examples that use paired-end sequencing, an unpaired read may result from a corresponding paired-end read failing to pass a quality threshold or otherwise being determined to be unusable.

A merged read 220 may include a combination of a sequence read and its paired-end read. For example, a merged read may include a pair of paired-end reads that have been merged together based on an overlapping portion of each of the paired-end reads in a pair. The pair of paired-end reads may be merged together by joining together the sequences of each of the paired-end reads in the pair to generate a merged sequence. The merged sequence may include a continuous sequence that includes non-overlapping portions of each of the paired-end reads 1A and 1B (illustrated as Mates 1A and 1B) and a sequence based on the overlapping portion. For example, a merged read 220 may be generated when an overlapping portion of paired-end reads 1A and 1B meets an overlapping criterion.

A concatenated unmerged read 230 may also include a combination of a sequence read and its paired-end read. However, unlike a merged read, a concatenated unmerged read 230 may be generated when the overlapping criterion has not been met. Thus, a concatenated unmerged read 230 may be generated based on a determination that both paired-end reads 2A and 2B (illustrated as Mates 2A and 2B) are available and are determined to not overlap based on the overlapping criterion. Because both paired-end reads 2A and 2B are determined not to overlap based on the overlapping criterion, an unmerged sequence may be generated by concatenating the sequence of one of the paired-end reads (such as 2B) onto the other paired-end read (such as 2A) (with or without using the complement of one to make both sequences the same strand/sense). Thus, further unlike merged reads, a sequence of a concatenated unmerged read will not include a portion deemed to overlap based on the overlap criterion. In some examples, the concatenated unmerged read 230 may be stored in association with an indication of the unmerged status in order to distinguish such concatenated unmerged reads from merged reads during analysis, as merged reads and concatenated unmerged reads may be analyzed by the system differently, as will be described herein. In some examples, an artificial sequence may be inserted in between the concatenated sequences of the paired-end reads 2A and 2B. The artificial sequence may include a predefined sequence, such as one or more nucleotide placeholders. The nucleotide placeholders may include a "N" or "n" to denote a placeholder, although other symbols or characters (other than actual nucleotide symbols such as A, C, G, T, and U) may be used. The artificial sequence may be 20 nucleotides in length, although other lengths may be used so long as the system is able to recognize such artificial sequence and/or the length thereof. Examples of concatenated unmerged reads 230 are respectively illustrated in FIGS. 5A-B.

Figures 3A, 3B, 3C:
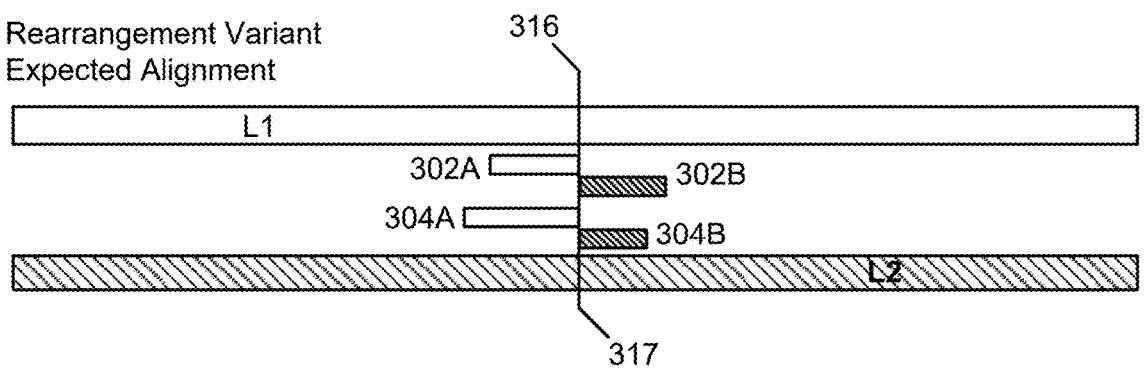
FIG. 3A illustrates an example of a deletion variant, according to an embodiment of the disclosure.
FIG. 3B illustrates an example of an insertion variant, according to an embodiment of the disclosure.
FIG. 3C illustrates an example of a rearrangement variant, according to an embodiment of the disclosure.

FIGS. 3A-3C respectively illustrate examples of variants and expected alignment of sequence reads 302, 304 to a reference sequence to detect the variants, according to an embodiment of the disclosure. Each of the FIGS. 3A-3C include a reference to a sequence read 302 and a sequence read 304. It should be understood that other numbers of sequence reads may be used as well. Furthermore, the sequence reads 302 and 304 may each refer to an unpaired read 210 (although some embodiments may omit unpaired reads 210 from variant detection), a merged read 220, an unmerged read, a concatenated unmerged read 230, and/or representative reads (which will be described with reference to FIGS. 4A-D) thereof.

FIG. 3A illustrates an example of a deletion variant, according to an embodiment of the disclosure. In this example, a deleted nucleic acid portion 301 has been deleted from a nucleic acid (such as a chromosome, genetic locus, etc.) in the sample 101. As such, the variant sequence will be missing the deleted nucleic acid portion 301. A first nucleic acid locus L1 and a second nucleic acid locus L2 may be brought closer together as a result of the deletion. The computer system 101 may detect the breakpoints 316 and 317 where the deletion occurred based on alignments of sequence reads 302 and 304 to the reference sequence at positions flanking the deleted nucleic acid portion 301. In particular, sequence reads 302 and 304 may be referred to herein as "split reads." For example, sequence read 302 may include a subsequence portion 302A that maps to a reference sequence up to the breakpoint 316 (assuming no loss of bases occurred) on the reference sequence and subsequence portion 302B that begins mapping to the reference sequence at the breakpoint 317 on the reference sequence. A breakpoint may refer to a position on a reference sequence at which a sequence read stops matching or starts matching, depending on the position of the sequence with respect to the variant and the nature of the variant.

FIG. 3B illustrates an example of an insertion variant, according to an embodiment of the disclosure. In this example, an inserted nucleic acid portion 303 has been inserted in the nucleic acid in the sample 101. As such, the first nucleic acid locus L1 and the second nucleic acid locus L2 spread further apart as a result of the insertion. The computer system 101 may detect breakpoint 316 based on alignments of sequence reads 302 and 304 to the reference sequence at a position prior to the insertion point. It should be noted that a first subsequence portion 302A may align to the reference sequence just before the insertion point at breakpoint 316. A second subsequence portion 302B may align to the inserted nucleic acid portion 303. Subsequence portions 304A and 304B may similarly align to the reference sequence and the inserted nucleic acid portion 303. Depending on the source of the inserted nucleic acid portion 303, the second subsequence portions 302B and 304B may align to the sequence of the second nucleic acid locus L2, to another sequence such as an intentionally inserted nucleic acid sequence inserted into the nucleic acid for therapeutic or other purposes, or other sequence that otherwise inserted into the nucleic acid at breakpoint 316.

FIG. 3C illustrates an example of a rearrangement variant, according to an embodiment of the disclosure. In this example, a first nucleic acid locus L1 is rearranged with a second nucleic acid locus L2. In an example, the first nucleic acid locus L1 may originate from a first portion such as chromosome of a genome and the second nucleic acid locus L2 may originate from a second portion such as another chromosome of the genome. In this example, the rearrangement may include an inter-chromosomal rearrangement. Other types of rearrangements, including intra-chromosomal rearrangements, inversions, and the like may occur and be detected by the computer system 110. The computer system 110 may detect the breakpoints 316 and 317 based on alignments of sequence reads 302 and 304 to the reference sequence at positions corresponding to the first nucleic locus L1 and the second nucleic locus L2.

FIG. 4 illustrates an example schematic data flow for generating representative reads, according to an embodiment of the disclosure. In the example illustrated in FIG. 4, paired-end reads of nine mated pairs are shown. Each of the paired-end reads may be sequenced from a polynucleotide molecule (and/or amplicon thereof) tagged by a molecular barcode on both ends. Such molecular barcodes are schematically shown as black, gray, and white boxes. It should be noted that some or all of the polynucleotide molecules may be amplified and sequenced without molecular barcode tagging as well or in the alternative.

The variant detection pipeline 130 may analyze the paired-end reads to merge, concatenate, and group the paired-end reads to generate representative reads for variant detection. For example, at 402, the merged read generator 132 may generate merged reads (shown as two boxes connected by a line) and the concatenated unmerged read generator 134 may generate concatenated unmerged reads (shown as two boxes connected by a line and a box labeled "NNN") to effectively generate longer sequence reads by combining paired-end reads.

To determine whether to generate merged reads from paired-end reads, the merged read generator 132 may align each paired-end read of a mate pair to a corresponding paired-end read of the mate pair to determine whether any alignment passes the overlap criterion.

The merged read generator 142 may merge paired-end reads to form a merged read when the overlap criterion is met. For example, both strands of the paired-end reads may be trimmed to remove at least a portion of the sequence at 3' ends in the overlapped region. For example, half of the sequence in the overlapped region at 3' ends can be removed to exclude bases with low sequence quality, molecular barcodes on 3' ends, and any mismatches. This may be useful in reducing sequencing errors. The merged read generator 132 may merge a sense strand of a paired-end read with an antisense strand of its corresponding paired-end read. For example, the merged read generator 142 may reorient the paired-end reads to be antiparallel and then merged to form a merged read or a paired-end read. The paired-end read or the merged read comprises the sense strand and the antisense strand having an overlapping region. As such, a merged read may represent a continuous sequence of a corresponding polynucleotide molecule that was sequenced. If the overlap criterion for a paired-end read of the paired-end reads is not met, the concatenated unmerged read generator 134 may concatenate unmerged reads (paired-end reads of a mate pair whose alignment did not satisfy the overlap criterion) by joining the respective sequences of the unmerged reads with an artificial sequence.

For example, the concatenated unmerged read generator 134 may join the paired-end reads to generate a concatenated unmerged read. The concatenated unmerged read generator 134 may generate an unmerged read in a manner similar to the way in which the merged read generator 132 generates a merged read, except that instead of merging a mated pair at an overlap region, the concatenated unmerged read generator 134 may join a mated pair with an artificial sequence, such as a series of twenty Ns, or other symbol as previously described at FIGS. 2A and 2B.

It should be noted that other sequencing techniques may be used as well, which may make merging or concatenating reads unnecessary or not possible. Furthermore, different sequencing techniques may be used in which pairs of sequences are generated for a given template (such as amplicons) and merged together based on the techniques disclosed herein. Alternatively, unique sequences (based on a combination of barcodes and internal sequence) are determined from among sets of paired-end reads. Then, the merged read generator 142 may merge the paired-end reads to generate representative merged, unique sequence reads.

At 404, the read family generator 136 may group the merged reads and/or the concatenated unmerged reads into one or more families. For example, the read family generator 136 may group the merged reads and/or the concatenated unmerged reads into families based on alignment (mapping) to one another, alignment to a reference sequence (where merged reads and/or concatenated unmerged reads that align to the same region of the reference sequence may be grouped together), based on unique molecular barcodes contained within the merged reads and concatenated unmerged reads, and/or other grouping criterion. In FIG. 4, only three families (A-C) each corresponding to a respective set of molecular barcodes is shown for illustrative clarity. Other numbers of families and compositions of paired-end reads in each family may be generated as well. As illustrated, Family A includes only merged reads, Family B includes a mix of merged and concatenated unmerged reads, and Family C includes only concatenated unmerged reads.

At 406, the read family generator 136 may select a representative read for each family. For example, a single merged read or a single concatenated unmerged read in a family may be selected to represent the family. Such selection may be based on quality of underlying sequence (as determined from the sequencing system 102), quality of alignment to a reference sequence, and/or other criterion. In another example, the read family generator 136 may determine a representative read based on a consensus of two or more underlying reads in the family. In some embodiments, the variant detector 138 may analyze the reference reads (and/or other reads described herein) to detect variants in the sample 101.

Figure 5A:
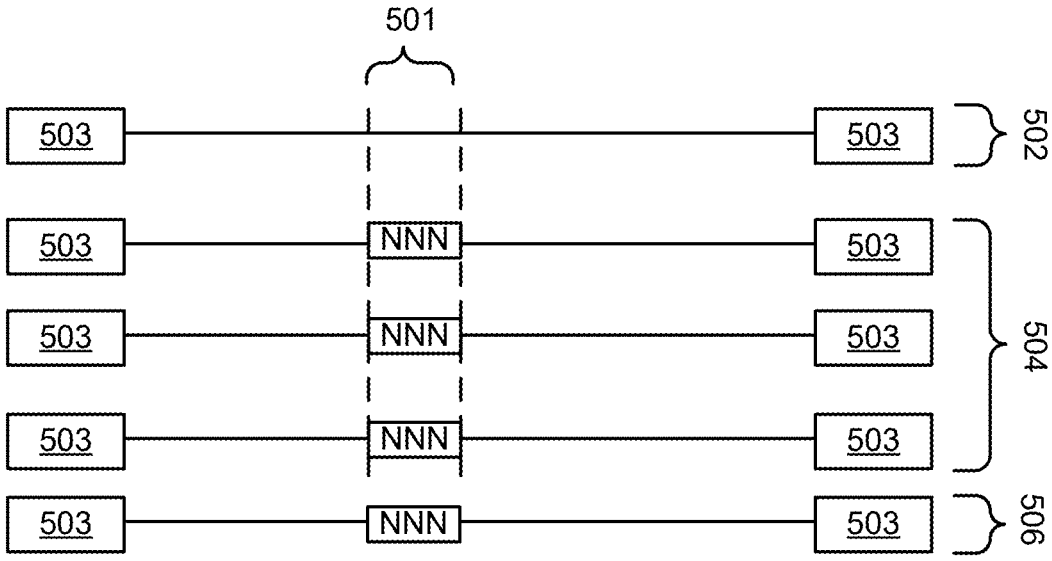
FIG. 5A-5B respectively illustrate examples of schematic diagrams for generating a representative sequence based on unmerged reads, according to an embodiment of the disclosure.

FIG. 5A illustrates an example schematic diagram for generating a representative sequence based on unmerged reads, according to an embodiment of the disclosure. As illustrated, a tagged molecule 502 tagged with molecular barcode 503 may be sequenced to generate pairs of paired-end reads (any intermediate amplicons are omitted for clarity), each of which are respectively concatenated to generate concatenated unmerged reads 504. When aligned to a reference sequence, none of the paired-end reads that are concatenated to form the concatenated unmerged reads 504 will cover region 501 on a reference sequence. Portions of the reference sequence outside region 501 may be covered by one or more of the concatenated unmerged reads 504.

The read family generator 136 may generate a grouped set for the concatenated unmerged reads 404 based on the molecular barcode 503 sequence shared by these concatenated unmerged reads 504 and/or based on alignment positions to the reference sequence. The read family generator 136 may generate a representative sequence 506 from among the grouped set. In the example illustrated in FIG. 5A, the representative sequence 506 may include a consensus sequence among overlapping regions of the paired-end reads with an artificial sequence inserted for the region 501. The concatenated unmerged read generator 134 may apply a coverage criterion that specifies a minimum coverage necessary to generate a consensus sequence in regions other than region 501 for the set. The coverage criterion may include other or additional requirements as well, such as one or more of the overlap criterion used by the merged read generator 132. The representative sequence 506, concatenated unmerged reads 504, and/or underlying paired-end reads may be used for variant detection, as will be described in FIGS. 6-8.

Figure 5B:
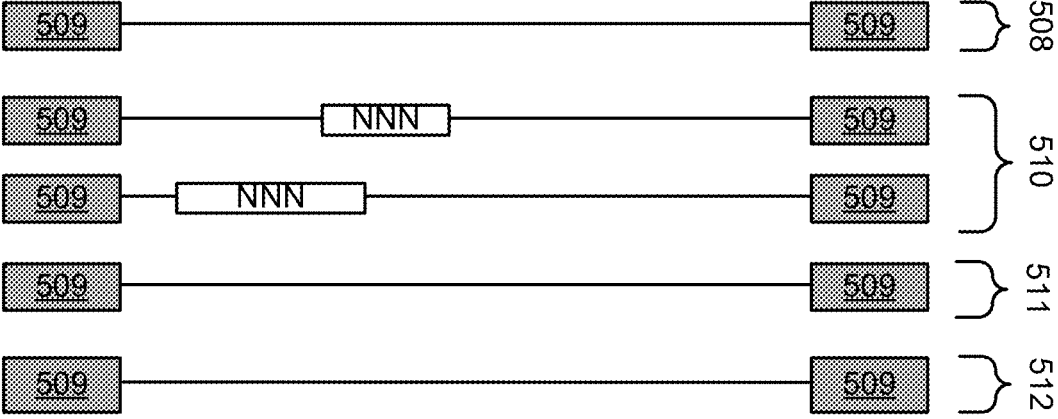

Referring now to FIG. 5B, in some instances, one or more concatenated unmerged reads 510 may together with one or more merged reads 511 may cover the sequence of a tagged polynucleotide molecule 508, which is tagged with a molecular barcode 509. In this example, sequence reads that were not merged with paired-ends may still be included with a set of merged reads to provide additional sequence coverage (such as for consensus calling or nucleotide disambiguation within a set or family). For example, a set of concatenated unmerged reads 510 generated from paired-end reads may have gaps that are covered by the sequence of other concatenated unmerged reads and/or the sequence of merged reads 511 also generated from the tagged polynucleotide molecule 509. Thus, the coverage criterion may be satisfied across the sequence of the set of concatenated unmerged reads. As such, the concatenated unmerged read generator 134 may generate a representative sequence 512 without artificial sequences. The representative sequence 512 and/or underlying reads may be used for variant detection, as will be described in FIGS. 6-8.

Variant Detection

Generally speaking, the variant detector 138 may analyze sequence reads directly from the sequence analysis pipeline 112 with or without merging by the merged read generator 132 and/or with or without generating concatenated unmerged reads by the concatenated unmerged read generator 134. In other words, the variant detector 138 may operate on individual reads, merged reads, representative (family consensus of) merged reads, concatenated unmerged reads, and/or representative (family consensus of) concatenated unmerged reads. The variant detector 138 may align the sequence reads to a reference sequence. For example, the variant detector 138 may perform the alignment using mapping tools, non-limiting examples of which may include Burrow's Wheeler Transform (BWA), Novoalign, Bowtie. The mapping tools may generate an alignment file describing alignment parameters used, position of the representative merged, unique reads (such as coordinates) on to the reference sequence and a quality score of mapping. The alignment parameters, such as number of differences allowed between the sequencing read and the reference sequence, number of gaps allowed and gap opening penalty, number of gap extensions, and the like, may be defined by a user. In one instance, BWA mapping tool with default alignment parameters is used to align the sequence reads to the reference sequence. BWA tool provides an output file, a BAM file that includes alignment statistics. Alignment statistics may include coordinates of the reference sequence to which the sequence reads align to. Alignment statistics may also provide a MapQ score to inform uniqueness of the sequence reads when mapped to the reference sequence. The sequence reads may then be sorted using the molecular barcodes and the coordinates on the reference sequence.

In some examples, the read family generator 136 may group the sequence reads into families. A family comprises reads originating from the same original tagged polynucleotide molecule. The sequence reads also have the same mapping coordinates on the reference sequence. For example, sequence reads having a pair of molecular barcodes, such as barcodes 404-406 and an endogenous sequence that aligns to the same coordinates on the reference sequence (e.g. 1300-1500 on chromosome 1) may be grouped into a family. In some embodiments, each family may be represented by a representative read. The representative read may include a sequence that is based on a consensus sequence of the family from which the representative read was generated (a "family consensus sequence"). The sequence reads may be added to the family if the sequence reads have the same molecular barcodes and at least one end position on the reference sequence similar to the rest of reads in the family. For example, the sequence reads may have the same molecular barcode and the same start position but stop positions may be within a predetermined nucleotide range. If the sequence reads have a same compacted stop sequence upon compaction, the sequence reads are grouped into the same family.

Similarly, the sequence reads may have the same molecular barcode and the same stop position but start positions may be within a predetermined nucleotide range. If the sequence reads have the same compacted start sequence upon compaction, the sequence reads are grouped into the same family. The sequence reads can be compacted to remove duplicate nucleotides in a homopolymer. Duplicate nucleotides in a homopolymer can be removed within a predetermined range of less than 2 nucleotides, 3 nucleotides, 4 nucleotides, 5 nucleotides, 6 nucleotides, 7 nucleotides, 8 nucleotides, 9 nucleotides, 10 nucleotides, 30 nucleotides, 30 nucleotides, 40 nucleotides, or 50 nucleotides. In some cases, the predetermined range can be less than 10 nucleotides. In some cases, the predetermined range can be less than 7 nucleotides. In some cases, the predetermined range can be less than 5 nucleotides. In some cases, the predetermined range can be less than 3 nucleotides. In one instance, the predetermined range is 4 nucleotides. Upon compaction, if at least 7 nucleotides in the end sequence map to the same position on the reference sequence as the rest of the representative merged, unique reads, then the compacted reads are grouped into the same family. Compacting of the merged reads reduces the number of families produced due to sequencing errors, for example, at the ends of a sequence read.

In certain embodiments, one or more homopolymers may be present at the start sequence and/or the stop sequence. The one or more homopolymers may be present anywhere in the sequence reads. In some embodiments, the homopolymers may comprise a poly(dA) or a poly(dT). In other embodiments, the homopolymers may comprise a poly(dG) or a poly(dC). As an example, for two sequence reads, if the start position of the first sequence read is within the predetermined range, such as less than 5 nucleotides, of the start position of the second sequence read and the first 7 bases of the compacted sequence of the first sequence read is identical to the first 7 bases of the compacted sequence of the second sequence read and the end positions of first sequence read and second sequence read are identical, then these reads can be grouped into the same family. Likewise, if the end position of the first sequence read is within the predetermined range, such as less than 5 nucleotides, of the end position of the second sequence read and the last 7 bases of the compacted sequence of the first sequence read is identical to the last 7 bases of the compacted sequence of the second sequence read and the start positions of first sequence read and second sequence read are identical, then these reads can be grouped into the same family.

Figure 6:
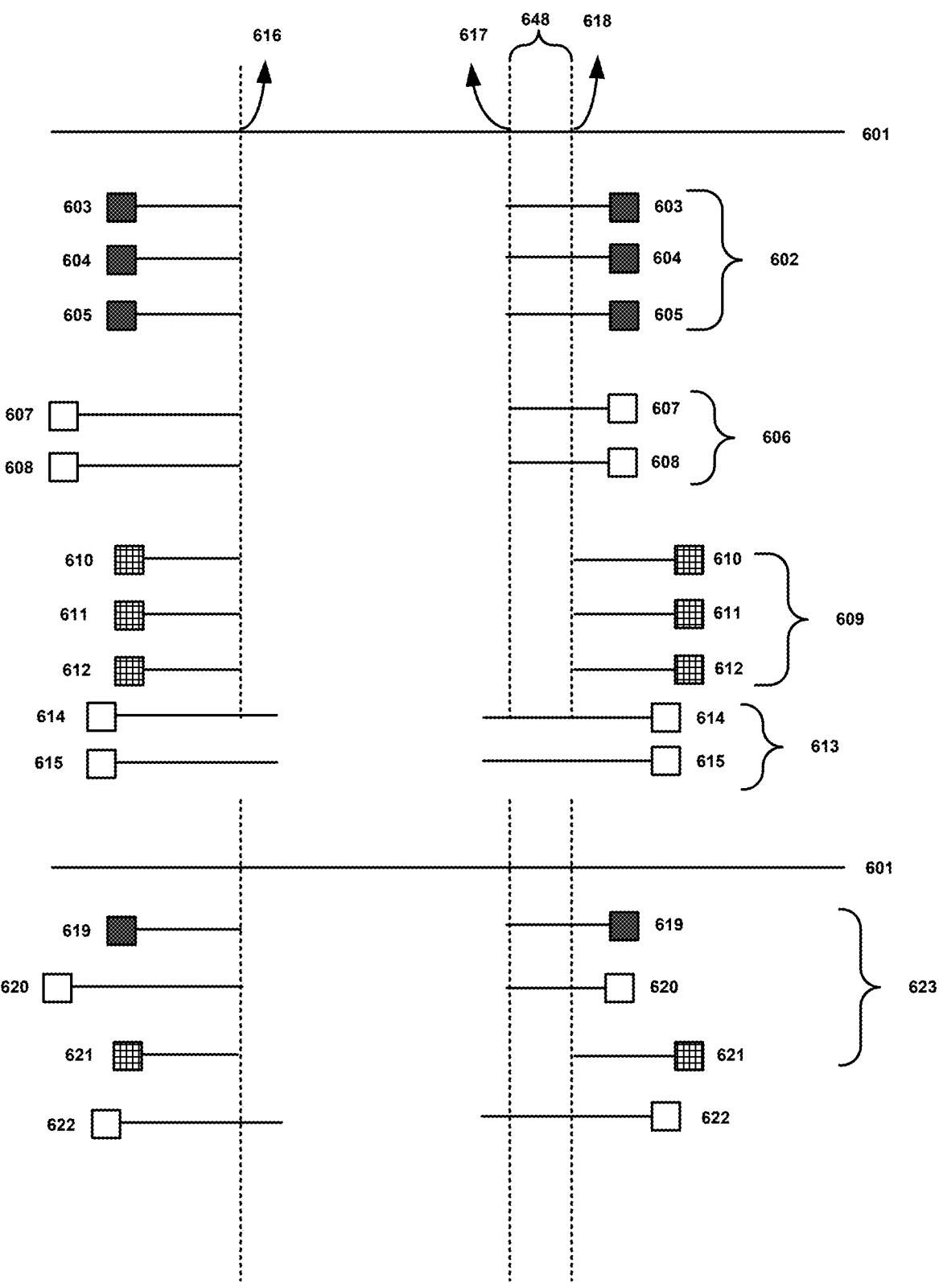
FIG. 6 illustrates a schematic diagram of determining a variant cluster, according to an embodiment of the disclosure.

FIG. 6 illustrates a schematic diagram of determining a variant cluster, according to an embodiment of the disclosure. As shown in FIG. 6, split reads within a family may be mapped to a reference sequence 601. A first family 602 comprises a first set of split reads 603, 604 and 605. A second family 606 comprises a second set of split reads 607 and 608. A third family 609 comprises a third set of split reads 610, 611 and 612. A fourth family 613 comprises a fourth set of split reads 614 and 615. Each of the split reads 603-605, 607, 608, 610-612, 614, and 615 may be an individual sequence read, an unpaired read, a merged read (or representative thereof), or a concatenated unmerged read (or representative thereof).

The first set of split reads and the second set of split reads map to nucleic acid loci adjacent to a first breakpoint pair 616 and 617. The third set of split reads map to nucleic acid loci adjacent a second breakpoint pair 616 and 618. The fourth set of split reads do not map to any nucleic acid loci adjacent to the breakpoints 616, 617 or 618.

In some embodiments, split read consensus sequences from families may cluster around a breakpoint pair and may form a variant cluster. A variant cluster may be a set of sequences that align to a reference sequence in a manner that suggests a breakpoint exists at a start of the alignment to the reference sequence, at the end of the alignment to the reference sequence, or certain distance from the start or end of the alignment to the reference sequence. For example, the first family 602 is represented by a first split read consensus sequence 619. The second family 606 is represented by a second split read consensus sequence 620. The third family 609 is represented by a third split read consensus sequence 621. The fourth family 513 is represented by a fourth split read consensus sequence 622. The first family 602, the second family 606 and the third family 609 cluster around the breakpoint pairs while the fourth family 613 does not.

In some embodiments, a variant cluster is detected based on mapping of consensus sequences on the breakpoint pairs. For example, the first split read consensus sequence 619, the second split read consensus sequence 620 and the third split read consensus sequence 621 form a variant cluster 623. However, the fourth split read consensus sequence 622 is not included in the variant cluster 623 because the distance between the respective breakpoints is greater than a predetermined breakpoint distance. These split read consensus sequences are included in the variant cluster in this embodiment because the distance between the respective breakpoints 648 is less than a predetermined breakpoint distance e.g., less than 10 nucleotides. Consensus breakpoints can be called based on, for example, the majority breakpoint in the variant clusters (breakpoints 616 and 617).

In other embodiments, families comprising split reads having similar breakpoint pairs may be grouped into variant clusters. For example, first family 602, second family 606 and third family 609 cluster around similar breakpoint pairs. These families are included in the variant cluster in this embodiment because the distance between the respective breakpoints 648 is less than a predetermined breakpoint distance e.g., less than 10 nucleotides. Consensus breakpoints can be called based on, for example, the majority breakpoint in the variant clusters.

Once the consensus breakpoint pair is identified, genetic variants, such as an insertion, deletion or fusion can be detected.

The variant detector 138 may distinguish between insertions and deletions (indels) from rearrangements such as gene fusions. For example, the variant detector 138 may take into consideration one or more factors including, but not limited to: (1) distance between the breakpoint pairs, (2) location of the breakpoints on the same chromosomes, (3) subsequences in the same or different orientation, and/or (4) subsequences in normal or reversed genomic order. If the breakpoints occur on different chromosomes, the variant would always be regarded as a fusion. If the breakpoints are on the same chromosome, but the subsequences are in different (opposing) 5'-3' orientation, the variant would also be regarded as fusion, or in some cases, an inversion. If the breakpoints are on the same chromosome and the subsequences are in the same 5'-3' orientation, the variant can be called an insertion or deletion if the distance between breakpoint pairs is less than a predetermined maximum distance (e.g., within a gene, less than 5,000 nucleotides, less than 4,000 nucleotides, less than 3,000 nucleotides, less than 2,000 nucleotides, or less than 1,000 nucleotides), otherwise it would be called as a fusion, or rearrangement. The insertions and deletions determined using the above criteria can be further distinguished from each other based on whether the subsequences are in normal genomic order (i.e., if the normal order of the subsequences on a chromosome is A-B, then, the order in the target molecules is also A-B—in such case call deletion) or in reversed genomic order (i.e., if the normal order of the subsequences on a chromosome is A-B, then, the order in the target molecules is B-A in such case call insertion). If the above rule established a deletion, the actual deleted sequence is between the two breakpoints. If the above rule established an insertion, a copy of the sequence between the two breakpoints is inserted next to one of the breakpoints (i.e., the sequence between the two breakpoints is duplicated). The subsequences may refer to the sequence of a split read within the families or a sequence of a family consensus sequence.

In some embodiments, the predetermined maximum distance between breakpoint pairs may be less than 5,000 nucleotides, less than 4,500 nucleotides, less than 4,000 nucleotides, less than 3,500 nucleotides, less than 3,000 nucleotides, less than 2,500 nucleotides, less than 2,000 nucleotides, less than 1,500 nucleotides, less than 1,000 nucleotides, less than 500 nucleotides, or less than 250 nucleotides. In some embodiments, the predetermined maximum distance between breakpoint pairs is less than the number of nucleotides of a region within a target gene of interest (e.g., less than the length of exon 14 in MET).

In certain embodiments, systems and methods disclosed herein are particularly useful for detecting midsize indels (such as those between 21-50 nucleotides, for example) and/or long indels (such as those greater than 50 nucleotides, greater than 100 nucleotides, greater than 500 nucleotides, greater than 1,000 nucleotides, greater than 2,000 nucleotides, greater than 3,000 nucleotides, greater than 4,000 nucleotides, greater than 5,000 nucleotides, greater than 10,000 nucleotides, an entire exon and/or intron, or an entire gene, for example).

In some embodiments, the insertion and/or deletion may occur within genes that include, but are not to be limited to, the group consisting of APC, ARID1A, ARID1B, ATM, BRCA1, BRCA2, CDH1, CDKN2A, EGFR, ERBB2, FMN2, GATA3, KIT, MET, MECP2, MLH1, MTOR, NF1, PDGFRA, PGAP3, PRODH, PTEN, RB1, SMAD4, SRD5A3, STK11, TP53, TSC1, VHL, and UBE3A. In some embodiments, the insertion and/or deletion may occur within genes that include, but are not to be limited to, EGFR (exons 18-21), ERBB2 (exons 19 and 20), ESR1 (exon 10), MET (exons 13-14 and intron 13-14), BRAF (exon 15), CTNNB1 (exon 3), FGFR2 (exon 6), GATA2 (exons 5-6), GNAS (exon 8), IDH1 (exon 4), IDH2 (exon 4), KIT (exons 1-21), KRAS (exons 2-3), NRAS (exons 2-3), PIK3CA (exon 10 and 21), PTEN (exon 5), SMAD4 (exon 12), TP53 (exons 4-8 and 11). In certain embodiments, the insertion and/or deletion may include, but not be limited to, a frameshift mutation, a non-frameshift mutation, an inversion (chromosomal rearrangement), whole exon deletions, and/or a tandem duplication.

In some embodiments, a fusion can be called when family consensus sequences comprised in a variant cluster fail to satisfy any or all of the criteria for calling an insertion and/or deletion.

The variant detector 138 may call an insertion, a deletion and/or a fusion by mapping sequence reads (such as individual reads, unpaired reads, merged reads (or representative sequences thereof), unmerged reads, and/or concatenated unmerged reads (or representative sequences thereof)) to a reference sequence and assigning a unique read identifier to the sequence read. Based on the alignment of the sequence reads, breakpoints and breakpoint pairs are determined on the reference sequence to determine the sequence reads having fusions. The breakpoints and the breakpoint pairs may be reported by breakpoint IDs and the number of the sequence reads aligned to the breakpoints and breakpoint pairs. The sequence reads having similar breakpoints are grouped into families based on common breakpoint pairs. The reads of families, or consensus sequences of the families, are then grouped into a variant cluster based on breakpoints within a predetermined breakpoint distance of each other. The predetermined breakpoint distance between the breakpoints in the reference sequence may be less than 25 nucleotides or less than 10 nucleotides or less than 5 nucleotides.

Figure 7A:
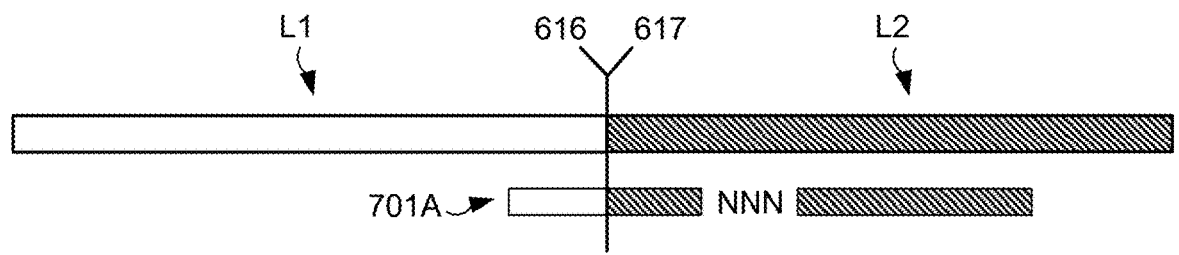
FIGS. 7A-7D respectively illustrate examples of using unmerged reads to detect variants, according to an embodiment of the disclosure.
Figure 7B:
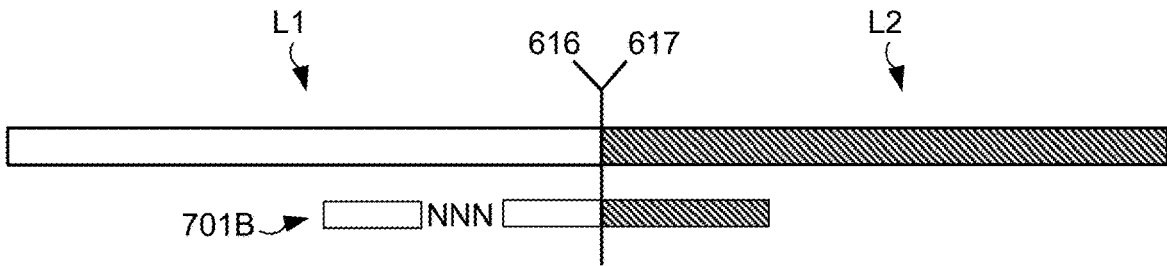
Figure 7C:
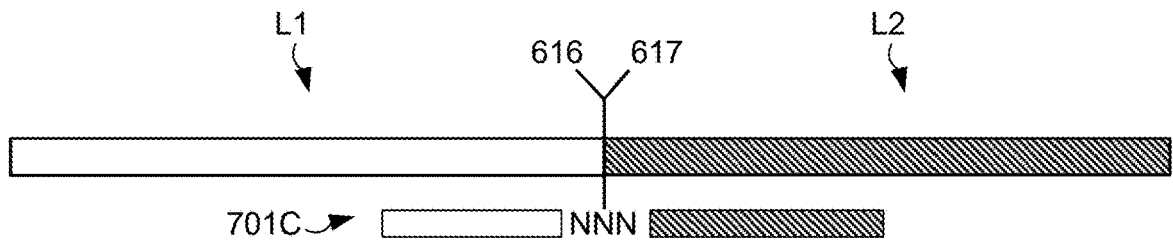

FIGS. 7A-7C respectively illustrate examples of using concatenated unmerged reads to detect variants, according to an embodiment of the disclosure. As illustrated in FIGS. 7A and 7B, breakpoint 616 and/or 617 (or other breakpoint) may be within the actual sequence (as opposed to artificial sequence) of a concatenated unmerged read 701A or 701B. In these examples, the concatenated unmerged reads 701A and 701B respectively shown in FIGS. 7A and 7B may be used to cluster reads and discover breakpoints as illustrated in FIG. 6.

As illustrated in FIG. 7C, the breakpoints 616 and 617 may be within the artificial sequence of a concatenated unmerged read. Even though a direct breakpoint may not be observed based on alignments of the concatenated unmerged read 701C to the reference sequence, the computer system 101 may use a concatenated unmerged read 701C in various ways. In some instances, each of the mates in the concatenated unmerged read may respectively align to nucleic acid loci L1 and L2 of the nucleic acid, suggesting that a rearrangement occurred if nucleic acid loci L1 and L2 are part of different chromosomes or other distinct nucleic acid molecules in the sample 101. If nucleic acid loci L1 and L2 are on the same chromosome or other nucleic acid molecule in the sample, and the mates of the concatenated unmerged read align to the reference sequence at distances greater than a predetermined number of nucleotides (such as greater than an expected size of molecules that were amplified and sequenced), then the computer system 101 may use the concatenated unmerged read 701C as evidence that an insertion exists between the paired-end reads of the concatenated unmerged read 701C. For example, the computer system 101 may use the concatenated unmerged read 701C as a criterion for calling an insertion (such as a criterion that one or more concatenated unmerged reads 701C that provide evidence for the insertion be present to call an insertion).

If nucleic acid loci L1 and L2 are on the same chromosome or other nucleic acid molecule in the sample, and the mates of the concatenated unmerged read align to the reference sequence at distances less than a predetermined number of nucleotides (such as less than an expected size of molecules that were amplified and sequenced), then the computer system 101 may use the concatenated unmerged read 701C as evidence that a deletion exists between the paired-end reads of the concatenated unmerged read 701C. For example, the computer system 101 may use the concatenated unmerged read 701C as a criterion for calling a deletion (such as a criterion that one or more concatenated unmerged reads 701C that provide evidence for the insertion be present to call a deletion).

Figure 7D:
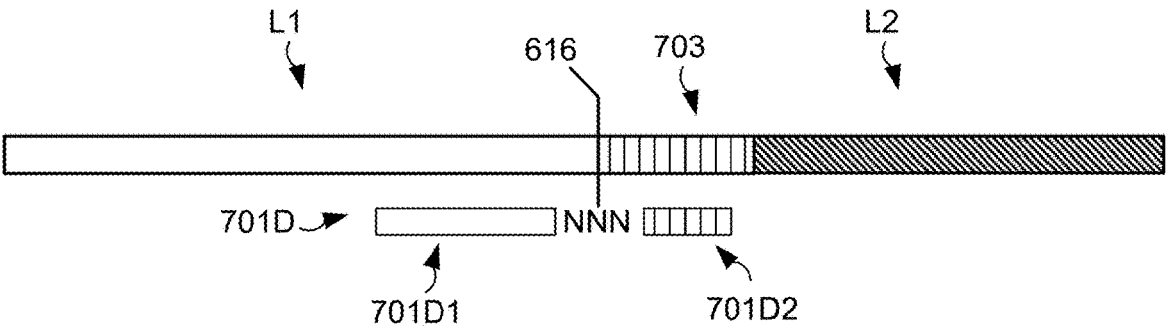

As illustrated in FIG. 7D, the breakpoints 616 and 617 may be within the artificial sequence of a concatenated unmerged read. In the concatenated unmerged read 701D, one portion or all of a paired-end read 701D1 may align to nucleic acid locus L1 while another portion or all of the other paired-end read 701D2 may not align to the reference sequence at all. In this example, an insertion sequence 703 may have been inserted into the nucleic acid molecule and the other paired-end read may align to the insertion sequence 703 (which may or may not be known). It should be understood that the insertion sequence 703 may be sufficiently small such that the other paired-end read 701D2 may align to a portion of nucleic acid locus L2 or other portion of the nucleic acid in the sample 101.

Figure 8:
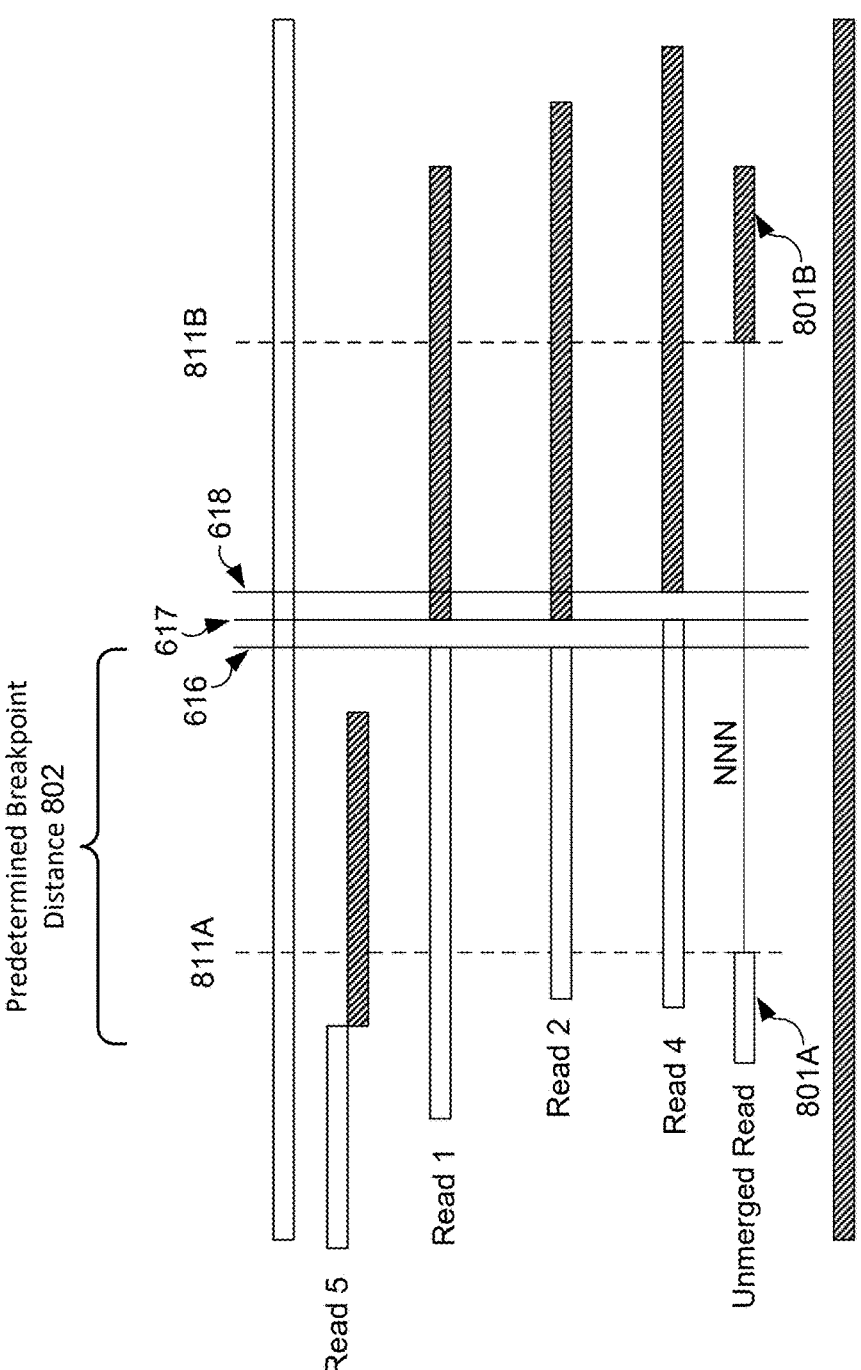
FIG. 8 illustrates an example of using an unmerged read to perform clustering on sequence reads, according to an embodiment of the disclosure.

Alternatively, or additionally, the computer system 110 may use concatenated unmerged reads to cluster sequence reads for variant detection, as illustrated in FIG. 8. FIG. 8 illustrates an example of using a concatenated unmerged read 801 (which may be a representative concatenated unmerged read or an individual concatenated unmerged read) to perform clustering on sequence reads 1-5, according to an embodiment of the disclosure. Reads 1-5 may each be a sequence read that includes a breakpoint 616, 617, and/or other breakpoint 618 within its nucleotide sequence, as determined from alignment with the reference sequence. Thus, reads 1-5 may include a unpaired read, a merged read, an unmerged read or another concatenated unmerged read (or consensus sequence of underlying reads).

In addition to or instead of using a predetermined breakpoint distance 802 to cluster sequence reads, the computer system 110 may use a concatenated unmerged read 801. For example, sequence reads 1-4 may be clustered together based on their alignment to the reference sequence falling between the paired-end reads 801A and 801B. For example, if a paired-end read 801A of the concatenated unmerged read 801 aligns to nucleic acid locus L1 and paired-end read 801B of the concatenated unmerged read 801 aligns to nucleic acid locus L2, and nucleic acid locus L1 and nucleic acid locus L2 are on different chromosomes or otherwise are not expected to align to both paired-end reads 801A and 801B of the concatenated unmerged read 801 (which may be based on an expected size of the molecule from which the paired-end reads 801A and 801B were sequenced), then the concatenated unmerged read 801 may support a conclusion that a rearrangement of the nucleic acid in the sample 101 exists. In this example, reads 1-4 may be clustered together because they include subsequences that align to nucleic acid locus L1 of the reference sequence at a position greater than the position 811A. Likewise, reads 1-4 may be clustered together because they include subsequences that align to nucleic acid locus L2 of the reference sequence at a position less than (or greater than depending on the sense of the reference sequence and the subsequence) of the position 811B. On the other hand, read 5 may not be clustered with reads 1-4 because read 5 aligns outside positions 811A and 811B.

Figure 9:
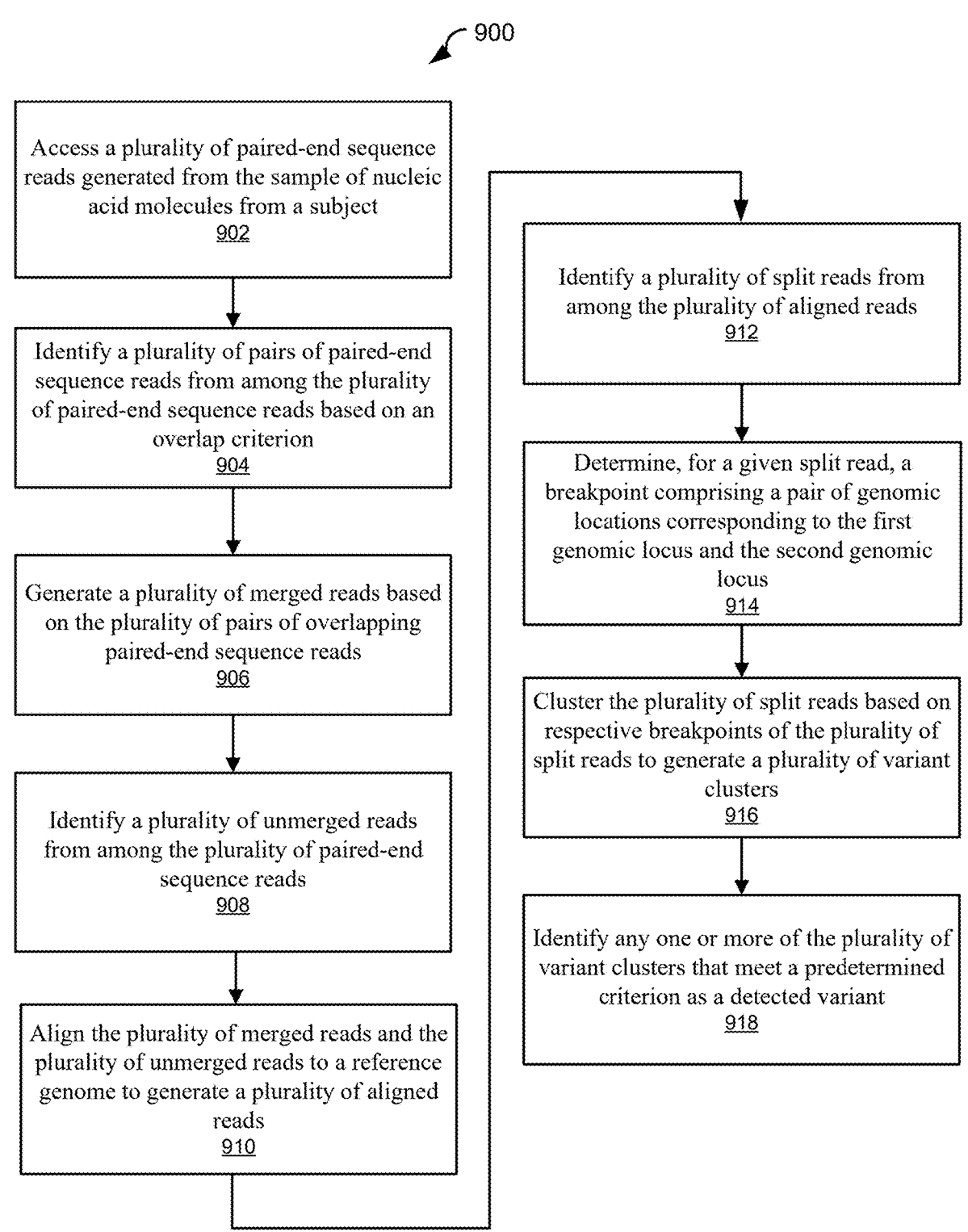
FIG. 9 illustrates an example method of detecting a variant in a sample, according to an embodiment of the disclosure.

FIG. 9 illustrates an example method 900 of detecting a variant in a sample, according to an embodiment of the disclosure. At 902, the method 900 may include accessing, by a computer system, a plurality of paired-end reads generated from the sample of nucleic acid molecules from the subject.

At 904, the method 900 may include identifying, by the computer system, a plurality of pairs of paired-end reads from among the plurality of paired-end reads based on an overlap criterion.

At 906, the method 900 may include generating, by the computer system, a plurality of merged reads based on the plurality of pairs of overlapping paired-end reads, wherein a merged read comprises a sequence based on respective sequences of a pair of overlapping paired-end reads.

At 908, the method 900 may include identifying, by the computer system, a plurality of concatenated unmerged reads from among the plurality of paired-end reads, wherein a given concatenated unmerged read comprises a paired-end read that does not satisfy an overlap criterion with a mated paired-end read.

At 910, the method 900 may include aligning, by the computer system, the plurality of merged reads and the plurality of concatenated unmerged reads to a reference genome to generate a plurality of aligned reads.

At 912, the method 900 may include identifying, by the computer system, a plurality of split reads from among the plurality of aligned reads, wherein a given split read includes a first subsequence portion that aligns to a first nucleic acid locus of the reference sequence and a second subsequence portion that aligns to a second nucleic acid locus of the reference sequence, the second nucleic acid locus different from the first nucleic acid locus.

At 914, the method 900 may include determining, by the computer system, for a given split read, a breakpoint comprising a pair of genomic locations corresponding to the first nucleic acid locus and the second nucleic acid locus.

At 916, the method 900 may include clustering, by the computer system, the plurality of split reads based on respective breakpoints of the plurality of split reads to generate a plurality of variant clusters.

At 918, the method 900 may include identifying, by the computer system, any one or more of the plurality of variant clusters that meet a predetermined criterion as indicative of a detected variant.

Figure 10:
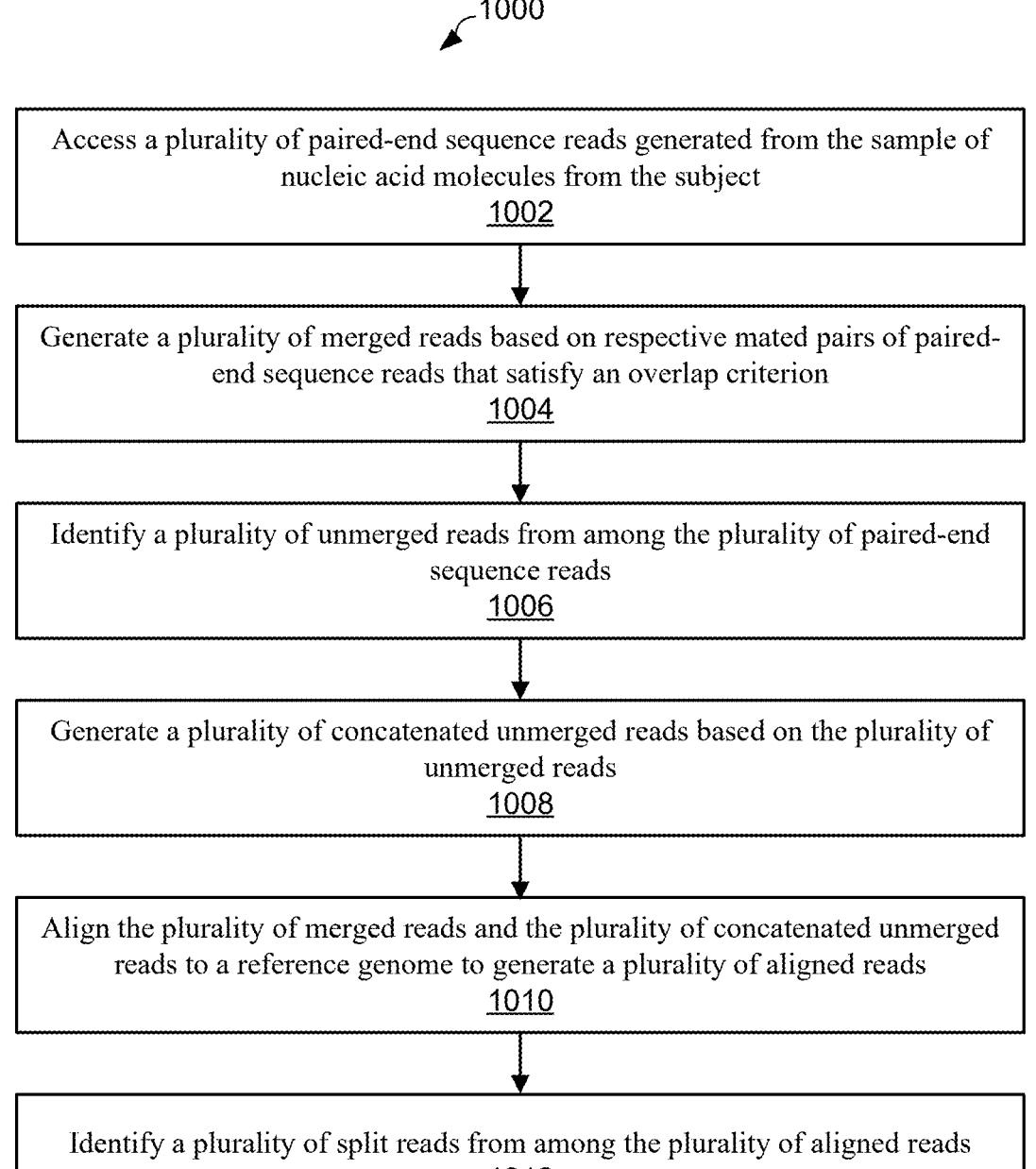
FIG. 10 illustrates another example method of detecting a variant in a sample, according to an embodiment of the disclosure.

FIG. 10 illustrates another example method 1000 of detecting a variant in a sample, according to an embodiment of the disclosure. At 1002, the method 1000 may include accessing a plurality of paired-end reads generated from the sample of nucleic acid molecules from the subject.

At 1004, the method 1000 may include generating a plurality of merged reads based on respective mated pairs of paired-end reads that satisfy an overlap criterion.

At 1006, the method 1000 may include identifying, by the computer system, a plurality of unmerged reads from among the plurality of paired-end reads, wherein a given unmerged read comprises a paired-end read that does not satisfy an overlap criterion with a corresponding mated paired-end read.

At 1008, the method 1000 may include generating a plurality of concatenated unmerged reads based on the plurality of unmerged reads. For example, the method 1000 may insert an artificial sequence in between the sequences of mated pairs of unmerged reads.

At 1010, the method 1000 may include aligning the plurality of merged reads and the plurality of concatenated unmerged reads to a reference genome to generate a plurality of aligned reads.

At 1012, the method 1000 may include identifying a plurality of split reads from among the plurality of aligned reads, wherein a given split read from among the plurality of split reads includes a first subsequence portion that aligns to a first nucleic acid locus of the reference sequence and a second subsequence portion that aligns to a second nucleic acid locus of the reference sequence, the second nucleic acid locus different from the first nucleic acid locus.

At 1014, the method 1000 may include identifying one or more variants based on the plurality of split reads.

The various processing operations 201-207, 902-918 and 1002-1014 and/or methods 200, 900 and 1000 respectively depicted in FIGS. 2A, 9 and 10 may be accomplished using some or all of the system components described in detail above and, in some implementations, various operations may be performed in different sequences and various operations may be omitted. Additional operations may be performed along with some or all of the operations shown in the depicted flow diagrams. One or more operations may be performed simultaneously. Accordingly, the operations as illustrated (and described in greater detail below) are provided as example and, as such, should not be viewed as necessarily limiting.

Although the embodiments described herein generally refer to examples of the use of paired-end sequencing, other embodiments may be directed to sequencing technology that do not use a paired-end technique in which individual sequence read lengths may be enhanced to increase sequence coverage for variant detection. For example, sequencing strategies in which the sequencing reads do not continuously cover a nucleic acid sequence may be extended using the techniques described herein, such as by concatenating the sequence reads. Such concatenation may be, for example, performed as described herein with respect to the concatenated unmerged reads. In a particular non-limiting example, nucleic acid sequence walking techniques may be employed in which gaps may result between sequence reads generated from primers directed to a nucleic acid sequence of interest to "walk" the nucleic acid sequence of interest. Various embodiments disclosed herein may be used to detect genetic variants in the nucleic acid of interest by concatenating the sequence reads and aligning them to a reference sequence of the nucleic acid sequence of interest to detect genetic variants as described herein. In other examples, the sequence reads may be merged together by even though they are not paired-end sequence reads since the primers may be expected to generate adjacent sequences.

Computer Implementation

The present methods can be computer-implemented, such that any or all of the steps described in the specification or appended claims other than wet chemistry steps can be performed in a suitable programmed computer. The computer can be a mainframe, personal computer, tablet, smart phone, cloud, online data storage, remote data storage, or the like. The computer can be operated in one or more locations.

Various operations of the present methods can utilize information and/or programs and generate results that are stored on computer-readable media (e.g., hard drive, auxiliary memory, external memory, server; database, portable memory device (e.g., CD-R, DVD, ZIP disk, flash memory cards), and the like.

The present disclosure also includes an article of manufacture for analyzing a nucleic acid population that includes a machine-readable medium containing one or more programs which when executed implement the steps of the present methods.

The disclosure can be implemented in hardware and/or software. For example, different aspects of the disclosure can be implemented in either client-side logic or server-side logic. The disclosure or components thereof can be embodied in a fixed media program component containing logic instructions and/or data that when loaded into an appropriately configured computing device cause that device to perform according to the disclosure. A fixed media containing logic instructions can be delivered to a viewer on a fixed media for physically loading into a viewer's computer or a fixed media containing logic instructions may reside on a remote server that a viewer accesses through a communication medium to download a program component.

The present disclosure provides computer control systems that are programmed to implement methods of the disclosure. The processor 120 may include a single core or multi core processor, or a plurality of processors for parallel processing. The storage device 122 may include random-access memory, read-only memory, flash memory, a hard disk, and/or other type of storage. The computer system 110 may include a communication interface (e.g., network adapter) for communicating with one or more other systems, and peripheral devices, such as cache, other memory, data storage and/or electronic display adapters. The components of the computer system 110 may communicate with one another through an internal communication bus, such as a motherboard. The storage device 122 may be a data storage unit (or data repository) for storing data. The computer system 110 may be operatively coupled to a computer network ("network") with the aid of the communication interface. The network may be the Internet, an internet and/or extranet, or an intranet and/or extranet that is in communication with the Internet. The network in some cases is a telecommunication and/or data network. The network may include a local area network. The network may include one or more computer servers, which can enable distributed computing, such as cloud computing. The network, in some cases with the aid of the computer system 110, may implement a peer-to-peer network, which may enable devices coupled to the computer system 120 to behave as a client or a server.

The processor 120 may execute a sequence of machine-readable instructions, which can be embodied in a program or software. The instructions may be stored in a memory location, such as the storage device 122. The instructions can be directed to the processor 120, which can subsequently program or otherwise configure the processor 120 to implement methods of the present disclosure. Examples of operations performed by the processor 120 may include fetch, decode, execute, and writeback.

The processor 120 may be part of a circuit, such as an integrated circuit. One or more other components of the system 100 may be included in the circuit. In some cases, the circuit may include an application specific integrated circuit (ASIC).

The storage device 122 may store files, such as drivers, libraries and saved programs. The storage device 122 can store user data, e.g., user preferences and user programs. The computer system 110 in some cases may include one or more additional data storage units that are external to the computer system 110, such as located on a remote server that is in communication with the computer system 110 through an intranet or the Internet.

The computer system 110 can communicate with one or more remote computer systems through the network. For instance, the computer system 110 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 110 via the network.

Methods as described herein can be implemented by way of machine (e.g., computer processor) executable code stored on an electronic storage location of the computer system 110, such as, for example, on the storage device 122. The machine executable or machine readable code can be provided in the form of software. During use, the code can be executed by the processor 905. In some cases, the code can be retrieved from the storage unit 915 and stored on the storage device 122 for ready access by the processor 120.

The code may be pre-compiled and configured for use with a machine having a processer adapted to execute the code, or can be compiled during runtime. The code can be supplied in a programming language that can be selected to enable the code to execute in a precompiled or as-compiled fashion.

Aspects of the systems and methods provided herein, such as the computer system 110, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk.

"Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible, storage media, "media" may include other types of (intangible) media.

"Storage" media, terms such as computer or machine "readable medium" refer to any tangible (such as physical), non-transitory, medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 110 can include or be in communication with an electronic display 935 that comprises a user interface (UI) for providing, for example, a report. Examples of UI's include, without limitation, a graphical user interface (GUI) and web-based user interface.

Methods and systems of the present disclosure can be implemented by way of one or more algorithms. An algorithm can be implemented by way of software upon execution by the processor 120.

Samples

A sample 101 may be any biological sample isolated from a subject. Samples can include body tissues, such as known or suspected solid tumors, whole blood, platelets, serum, plasma, stool, red blood cells, white blood cells or leucocytes, endothelial cells, tissue biopsies, cerebrospinal fluid synovial fluid, lymphatic fluid, ascites fluid, interstitial or extracellular fluid, the fluid in spaces between cells, including gingival crevicular fluid, bone marrow, pleural effusions, cerebrospinal fluid, saliva, mucous, sputum, semen, sweat, urine. Samples are preferably body fluids, particularly blood and fractions thereof, and urine. Such samples include nucleic acids shed from tumors. The nucleic acids can include DNA and RNA and can be in double- and/or single-stranded forms. A sample can be in the form originally isolated from a subject or can have been subjected to further processing to remove or add components, such as cells, enrich for one component relative to another, or convert one form of nucleic acid to another, such as RNA to DNA or single-stranded nucleic acids to double-stranded. Thus, for example, a body fluid for analysis is plasma or serum containing cell-free nucleic acids, e.g., cell-free DNA (cfDNA).

In some embodiments, the sample volume of body fluid taken from a subject depends on the desired read depth for sequenced regions. Exemplary volumes are about 0.4-40 ml, about 5-20 ml, about 10-20 ml. For example, the volume can be about 0.5 ml, about 1 ml, about 5 ml, about 10 ml, about 20 ml, about 30 ml, about 40 ml, or more milliliters. A volume of sampled plasma is typically between about 5 ml to about 20 ml.

The sample can comprise various amounts of nucleic acid. Typically, the amount of nucleic acid in a given sample is equated with multiple genome equivalents. For example, a sample of about 30 ng DNA can contain about 10,000 ($10^4$) haploid human genome equivalents and, in the case of cfDNA, about 200 billion ($2 \times 10^{11}$) individual polynucleotide molecules. Similarly, a sample of about 100 ng of DNA can contain about 30,000 haploid human genome equivalents and, in the case of cfDNA, about 600 billion individual molecules.

In some embodiments, a sample comprises nucleic acids from different sources, e.g., from cells and from cell-free sources (e.g., blood samples, etc.). Typically, a sample includes nucleic acids carrying mutations. For example, a sample optionally comprises DNA carrying germline mutations and/or somatic mutations. Typically, a sample comprises DNA carrying cancer-associated mutations (e.g., cancer-associated somatic mutations).

Exemplary amounts of cell-free nucleic acids in a sample before amplification typically range from about 1 femtogram (fg) to about 1 microgram (µg), e.g., about 1 picogram (pg) to about 200 nanogram (ng), about 1 ng to about 100 ng, about 10 ng to about 1000 ng. In some embodiments, a sample includes up to about 600 ng, up to about 500 ng, up to about 400 ng, up to about 300 ng, up to about 200 ng, up to about 100 ng, up to about 50 ng, or up to about 20 ng of cell-free nucleic acid molecules. Optionally, the amount is at least about 1 fg, at least about 10 fg, at least about 100 fg, at least about 1 pg, at least about 10 pg, at least about 100 pg, at least about 1 ng, at least about 10 ng, at least about 100 ng, at least about 150 ng, or at least about 200 ng of cell-free nucleic acid molecules. In certain embodiments, the amount is up to about 1 fg, about 10 fg, about 100 fg, about 1 pg, about 10 pg, about 100 pg, about 1 ng, about 10 ng, about 100 ng, about 150 ng, or about 200 ng of cell-free nucleic acid molecules. In some embodiments, methods include obtaining between about 1 fg to about 200 ng cell-free nucleic acid molecules from samples.

Cell-free nucleic acids typically have a size distribution of between about 100 nucleotides in length and about 500 nucleotides in length, with molecules of about 110 nucleotides in length to about 230 nucleotides in length representing about 90% of molecules in the sample, with a mode of about 168 nucleotides in length and a second minor peak in a range between about 240 to about 440 nucleotides in length. In certain embodiments, cell-free nucleic acids are from about 160 to about 180 nucleotides in length, or from about 320 to about 360 nucleotides in length, or from about 440 to about 480 nucleotides in length.

In some embodiments, cell-free nucleic acids are isolated from bodily fluids through a partitioning step in which cell-free nucleic acids, as found in solution, are separated from intact cells and other non-soluble components of the bodily fluid. In some of these embodiments, partitioning includes techniques such as centrifugation or filtration. Alternatively, cells in bodily fluids are lysed, and cell-free and cellular nucleic acids processed together. Generally, after addition of buffers and wash steps, cell-free nucleic acids are precipitated with, for example, an alcohol. In certain embodiments, additional clean up steps are used, such as silica-based columns to remove contaminants or salts. Non-specific bulk carrier nucleic acids, for example, are optionally added throughout the reaction to optimize certain aspects of the exemplary procedure, such as yield. After such processing, samples typically include various forms of nucleic acids including double-stranded DNA, single-stranded DNA and/or single-stranded RNA. Optionally, single stranded DNA and/or single stranded RNA are converted to double stranded forms so that they are included in subsequent processing and analysis steps.

Nucleic Acid Tags

In some embodiments, the nucleic acid molecules (from the sample of polynucleotides) may be tagged with sample indexes and/or molecular barcodes (referred to generally as "tags"). Tags may be incorporated into or otherwise joined to adapters by chemical synthesis, ligation (e.g., blunt-end ligation or sticky-end ligation), or overlap extension polymerase chain reaction (PCR), among other methods. Such adapters may be ultimately joined to the target nucleic acid molecule. In other embodiments, one or more rounds of amplification cycles (e.g., PCR amplification) are generally applied to introduce sample indexes to a nucleic acid molecule using conventional nucleic acid amplification methods. The amplifications may be conducted in one or more reaction mixtures (e.g., a plurality of microwells in an array). Molecular barcodes and/or sample indexes may be introduced simultaneously, or in any sequential order. In some embodiments, molecular barcodes and/or sample indexes are introduced prior to and/or after sequence capturing steps are performed. In some embodiments, only the molecular barcodes are introduced prior to probe capturing and the sample indexes are introduced after sequence capturing steps are performed. In some embodiments, both the molecular barcodes and the sample indexes are introduced prior to performing probe-based capturing steps. In some embodiments, the sample indexes are introduced after sequence capturing steps are performed. In some embodiments, molecular barcodes are incorporated to the nucleic acid molecules (e.g. cfDNA molecules) in a sample through adapters via ligation (e.g., blunt-end ligation or sticky-end ligation). In some embodiments, sample indexes are incorporated to the nucleic acid molecules (e.g. cfDNA molecules) in a sample through overlap extension polymerase chain reaction (PCR). Typically, sequence capturing protocols involve introducing a single-stranded nucleic acid molecule complementary to a targeted nucleic acid sequence, e.g., a coding sequence of a genomic region and mutation of such region is associated with a cancer type.

In some embodiments, the tags may be located at one end or at both ends of the sample nucleic acid molecule. In some embodiments, tags are predetermined or random or semi-random sequence oligonucleotides. In some embodiments, the tags may be less than about 500, 200, 100, 50, 20, 10, 9, 8, 7, 6, 5, 4, 3, 2, or 1 nucleotides in length. The tags may be linked to sample nucleic acids randomly or non-randomly.

In some embodiments, each sample is uniquely tagged with a sample index or a combination of sample indexes. In some embodiments, each nucleic acid molecule of a sample or sub-sample is uniquely tagged with a molecular barcode or a combination of molecular barcodes. In other embodiments, a plurality of molecular barcodes may be used such that molecular barcodes are not necessarily unique to one another in the plurality (e.g., non-unique molecular barcodes). In these embodiments, molecular barcodes are generally attached (e.g., by ligation) to individual molecules such that the combination of the molecular barcode and the sequence it may be attached to creates a unique sequence that may be individually tracked. Detection of non-uniquely tagged molecular barcodes in combination with endogenous sequence information (e.g., the beginning (start) and/or end (stop) portions corresponding to the sequence of the original nucleic acid molecule in the sample, sub-sequences of sequence reads at one or both ends, length of sequence reads, and/or length of the original nucleic acid molecule in the sample) typically allows for the assignment of a unique identity to a particular molecule. The length, or number of base pairs, of an individual sequence read are also optionally used to assign a unique identity to a given molecule. As described herein, fragments from a single strand of nucleic acid having been assigned a unique identity, may thereby permit subsequent identification of fragments from the parent strand, and/or a complementary strand.

In some embodiments, molecular barcodes are introduced at an expected ratio of a set of molecular barcodes (e.g., a combination of unique or non-unique molecular barcodes) to molecules in a sample. One example format uses from about 2 to about 1,000,000 different molecular barcodes ligated to both ends of a target molecules, or from about 5 to about 150 different molecular barcodes, or from about 20 to about 50 different molecular barcodes. Alternatively, from about 25 to about 1,000,000 different molecular barcodes may be used.

For example, 20-50 molecular barcodes at each end of the target molecules. Such numbers of identifiers are typically sufficient for different molecules having the same start and stop points to have a high probability (e.g., at least 94%, 99.5%, 99.99%, or 99.999%) of receiving different combinations of identifiers. In some embodiments, about 80%, about 90%, about 95%, or about 99% of molecules have the same combinations of molecular barcodes.

In some embodiments, the assignment of unique or non-unique molecular barcodes in reactions is performed using methods and systems described in, for example, U.S. patents application Nos. 20010053519, 20030152490, and 20110160078, and U.S. Pat. Nos. 6,582,908, 7,537,898, 9,598,731, and 9,902,992, each of which is hereby incorporated by reference in its entirety. Alternatively, in some embodiments, different nucleic acid molecules of a sample may be identified using only endogenous sequence information (e.g., start and/or stop positions, sub-sequences of one or both ends of a sequence, and/or lengths).

Nucleic Acid Amplification

Sample nucleic acids flanked by adapters are typically amplified by PCR and other amplification methods using nucleic acid primers binding to primer binding sites in adapters flanking a DNA molecule to be amplified. In some embodiments, amplification methods involve cycles of extension, denaturation and annealing resulting from thermocycling, or can be isothermal as, for example, in transcription mediated amplification. Other exemplary amplification methods that are optionally utilized, include the ligase chain reaction, strand displacement amplification, nucleic acid sequence-based amplification, and self-sustained sequence-based replication, among other approaches.

One or more rounds of amplification cycles are generally applied to introduce sample indexes to a nucleic acid molecule using conventional nucleic acid amplification methods. The amplifications are typically conducted in one or more reaction mixtures. Molecular tags and sample indexes/tags are optionally introduced simultaneously, or in any sequential order. In some embodiments, molecular tags and sample indexes are introduced prior to and/or after nucleic acid enrichment are performed. In some embodiments, only the molecular tags are introduced prior to probe capturing and the sample indexes are introduced after nucleic acid enrichment is performed. In certain embodiments, both the molecular tags and the sample indexes/tags are introduced prior to performing probe-based capturing steps. In some embodiments, the sample indexes/tags are introduced after sequence capturing steps are performed. Typically, sequence capturing protocols involve introducing a single-stranded nucleic acid molecule complementary to a targeted nucleic acid sequence, e.g., a coding sequence of a genomic region and mutation of such region associated with a cancer type. Typically, the amplification reactions generate a plurality of non-uniquely or uniquely tagged nucleic acid amplicons with molecular tags and sample indexes/tags at size ranging from about 200 nucleotides (nt) to about 700 nt, from 250 nt to about 350 nt, or from about 320 nt to about 550 nt. In some embodiments, the amplicons have a size of about 300 nt. In some embodiments, the amplicons have a size of about 500 nt.

Nucleic Acid Enrichment

In some embodiments, sequences are enriched prior to sequencing the nucleic acids. Enrichment is optionally performed for specific target regions. In some embodiments, targeted regions of interest may be enriched with nucleic acid capture probes ("baits") selected for one or more bait set panels using a differential tiling and capture scheme. A differential tiling and capture scheme generally uses bait sets of different relative concentrations to differentially tile (e.g., at different "resolutions") across genomic regions associated with the baits, subject to a set of constraints (e.g., sequencer constraints such as sequencing load, utility of each bait, etc.), and capture the targeted nucleic acids at a desired level for downstream sequencing. These targeted genomic regions of interest optionally include natural or synthetic nucleotide sequences of the nucleic acid construct. In some embodiments, biotin-labeled beads with probes to one or more regions of interest can be used to capture target sequences, and optionally followed by amplification of those regions, to enrich for the regions of interest.

Sequence capture typically involves the use of oligonucleotide probes that hybridize to the target nucleic acid sequence. In certain embodiments, a probe set strategy involves tiling the probes across a region of interest. Such probes can be, for example, from about 60 to about 120 nucleotides in length. The set can have a depth of about 2× or more, 3× or more, 4× or more, 5× or more, 6× or more, 7× or more, 8× or more, 9× or more, 10× or more, 15× or more, 20× or more, 50× or more. The effectiveness of sequence capture generally depends, in part, on the length of the sequence in the target molecule that is complementary (or nearly complementary) to the sequence of the probe.

Nucleic Acid Sequencing

Sample nucleic acids flanked by adapters with or without prior amplification can be subject to sequencing, such as by one or more sequencing devices 107. Sequencing methods include, for example, Sanger sequencing, high-throughput sequencing, pyrosequencing, sequencing-by-synthesis, single-molecule sequencing, nanopore sequencing, semi-conductor sequencing, sequencing-by-ligation, sequencing-by-hybridization, RNA-Seq (Illumina), Digital Gene Expression (Helicos), Next generation sequencing, Single Molecule Sequencing by Synthesis (SMSS) (Helicos), massively-parallel sequencing, Clonal Single Molecule Array (Solexa), shotgun sequencing, Ion Torrent, Oxford Nanopore, Roche Genia, Maxim-Gilbert sequencing, primer walking, sequencing using PacBio, SOLID, Ion Torrent, or Nanopore platforms. Sequencing reactions can be performed in a variety of sample processing units, which may be multiple lanes, multiple channels, multiple wells, or other means of processing multiple sample sets substantially simultaneously. Sample processing unit can also include multiple sample chambers to enable processing of multiple runs simultaneously.

The sequencing reactions can be performed on one or more fragments types known to contain markers of cancer of other disease. The sequencing reactions can also be performed on any nucleic acid fragments present in the sample. The sequence reactions may provide for sequence coverage of the genome of at least 5%, 10%, 15%, 20%, 25%, 30%, 40%, 50%, 60%, 70%, 80%, 90%, 95%, 99%, 99.9% or 100%. In other cases, sequence coverage of the genome may be less than 5%, 10%, 15%, 20%, 25%, 30%, 40%, 50%, 60%, 70%, 80%, 90%, 95%, 99%, 99.9% or 100%.

Simultaneous sequencing reactions may be performed using multiplex sequencing. In some cases, cell free polynucleotides may be sequenced with at least 1000, 2000, 3000, 4000, 5000, 6000, 7000, 8000, 9000, 10000, 50000, 100,000 sequencing reactions. In other cases, cell free polynucleotides may be sequenced with less than 1000, 2000, 3000, 4000, 5000, 6000, 7000, 8000, 9000, 10000, 50000, 100,000 sequencing reactions. Sequencing reactions may be performed sequentially or simultaneously. Subsequent data analysis may be performed on all or part of the sequencing reactions. In some cases, data analysis may be performed on at least 1000, 2000, 3000, 4000, 5000, 6000, 7000, 8000, 9000, 10000, 50000, 100,000 sequencing reactions. In other cases, data analysis may be performed on less than 1000, 2000, 3000, 4000, 5000, 6000, 7000, 8000, 9000, 10000, 50000, 100,000 sequencing reactions. An exemplary read depth from 1000-50000 reads per locus (base).

Sequence Analysis Pipeline

The present methods can be used to diagnose presence of conditions, particularly cancer, in a subject, to characterize conditions (e.g., staging cancer or determining heterogeneity of a cancer), monitor response to treatment of a condition, effect prognosis risk of developing a condition or subsequent course of a condition.

Various cancers may be detected using the present methods. Cancers cells, as most cells, can be characterized by a rate of turnover, in which old cells die and replaced by newer cells. Generally dead cells, in contact with vasculature in a given subject, may release DNA or fragments of DNA into the blood stream. This is also true of cancer cells during various stages of the disease. Cancer cells may also be characterized, dependent on the stage of the disease, by various genetic aberrations such as copy number variation as well as rare mutations. This phenomenon may be used to detect the presence or absence of cancers individuals using the methods and systems described herein.

The types and number of cancers that may be detected may include blood cancers, brain cancers, lung cancers, skin cancers, nose cancers, throat cancers, liver cancers, bone cancers, lymphomas, pancreatic cancers, skin cancers, bowel cancers, rectal cancers, thyroid cancers, bladder cancers, kidney cancers, mouth cancers, stomach cancers, solid state tumors, heterogeneous tumors, homogenous tumors and the like.

Cancers can be detected from genetic variations including mutations, rare mutations, indels, copy number variations, transversions, translocations, inversion, deletions, aneuploidy, partial aneuploidy, polyploidy, chromosomal instability, chromosomal structure alterations, gene fusions, chromosome fusions, gene truncations, gene amplification, gene duplications, chromosomal lesions, DNA lesions, abnormal changes in nucleic acid chemical modifications, abnormal changes in epigenetic patterns.

Genetic data can also be used for characterizing a specific form of cancer. Cancers are often heterogeneous in both composition and staging. Genetic profile data may allow characterization of specific sub-types of cancer that may be important in the diagnosis or treatment of that specific sub-type. This information may also provide a subject or practitioner clues regarding the prognosis of a specific type of cancer and allow either a subject or practitioner to adapt treatment options in accord with the progress of the disease. Some cancers progress, becoming more aggressive and genetically unstable. Other cancers may remain benign, inactive or dormant. The system and methods of this disclosure may be useful in determining disease progression.

The present analysis is also useful in determining the efficacy of a particular treatment option. Successful treatment options may increase the amount of copy number variation or rare mutations detected in a subject's blood if the treatment is successful as more cancers may die and shed DNA. In other examples, this may not occur. In another example, perhaps certain treatment options may be correlated with genetic profiles of cancers over time. This correlation may be useful in selecting a therapy. Additionally, if a cancer is observed to be in remission after treatment, the present methods can be used to monitor residual disease or recurrence of disease.

The present methods can also be used for detecting genetic variations in conditions other than cancer. Immune cells, such as B cells, may undergo rapid clonal expansion upon the presence certain diseases. Clonal expansions may be monitored using copy number variation detection and certain immune states may be monitored. In this example, copy number variation analysis may be performed over time to produce a profile of how a particular disease may be progressing. Copy number variation or even rare mutation detection may be used to determine how a population of pathogens are changing during the course of infection. This may be particularly important during chronic infections, such as HIV/AIDS or Hepatitis infections, whereby viruses may change life cycle state and/or mutate into more virulent forms during the course of infection. The present methods may be used to determine or profile rejection activities of the host body, as immune cells attempt to destroy transplanted tissue to monitor the status of transplanted tissue as well as altering the course of treatment or prevention of rejection.

Further, the methods of the disclosure may be used to characterize the heterogeneity of an abnormal condition in a subject, the method comprising generating a genetic profile of extracellular polynucleotides in the subject, wherein the genetic profile comprises a plurality of data resulting from copy number variation and rare mutation analyses. In some cases, including but not limited to cancer, a disease may be heterogeneous. Disease cells may not be identical. In the example of cancer, some tumors are known to comprise different types of tumor cells, some cells in different stages of the cancer. In other examples, heterogeneity may comprise multiple foci of disease. Again, in the example of cancer, there may be multiple tumor foci, perhaps where one or more foci are the result of metastases that have spread from a primary site.

The present methods can be used to generate or profile, fingerprint or set of data that is a summation of genetic information derived from different cells in a heterogeneous disease. This set of data may comprise copy number variation and rare mutation analyses alone or in combination.

The present methods can be used to diagnose, prognose, monitor or observe cancers or other diseases of fetal origin. That is, these methodologies may be employed in a pregnant subject to diagnose, prognose, monitor or observe cancers or other diseases in an unborn subject whose DNA and other polynucleotides may co-circulate with maternal molecules.

Precision Treatment Examples

The precision diagnostics provided by the improved computer system 110 may result in precision treatment plans, which may be identified by the computer system 110 (and/or curated by health professionals).

The number and types of nucleic acid variants in a sample can provide an indication of the amenability of the subject providing the sample to treatment, i.e., therapeutic intervention. For example, presence of a high number of nucleic acid variants is a positive indicator for immunotherapy because the presence of such mutation is associated with neoepitopes forming targets for immunotherapy. Immunotherapy can include use of an antibody against any of PD-1, PD-2, PD-L1, PD-L2, CTLA-40, OX40, B7.1, B7He, LAG3, CD137, KIR, CCR5, CD27, or CD40 among other treatments. Other exemplary agents for immunotherapy include proinflammatory cytokines, such as IL-1B, IL-6, and TNF-α. Other exemplary agents are T-cells activated against a tumor, such as by expressing of a chimeric antigen targeting a tumor antigen from the T-cell. Immunotherapy stimulates the immune system to attack tumor antigens distinguished from wildtype counterparts by the presence of mutation(s).

Other treatment options include administration of a targeted therapy for a particular variant. For example, a targeted therapy for nucleic acid rearrangements (e.g., EGFR or ALK fusions) may include tyrosine kinase inhibitors, such as erlotinib, afatinib, alectinib, brigatinib, ceritinib, cetuximab, crizotinib, ensartinib, laroterctinib, lenvatinib, lorlatinib, osimertinib, pazopanib, regorafenib, and TPX-0005.

Nucleic acid variants in sequenced nucleic acids can be determined by comparing sequenced nucleic acids with a reference sequence. The reference sequence is often a known sequence, e.g., a known whole or partial genome sequence from an object, whole genome sequence of a human object. The reference sequence can be hG19. The sequenced nucleic acids can represent sequences determined directly for a nucleic acid in a sample, or a consensus of sequences of amplification products of such a nucleic acid, as described above. A comparison can be performed at one or more designated positions on a reference sequence. A subset of sequenced nucleic acids can be identified including a position corresponding with a designated position of the reference sequence when the respective sequences are maximally aligned. Within such a subset it can be determined which, if any, sequenced nucleic acids include a nucleotide variation at the designated position, and optionally which if any, include a reference nucleotide (i.e., same as in the reference sequence). If the number of sequenced nucleic acids in the subset including a nucleotide variant exceeds a threshold, then a variant nucleotide can be called at the designated position. The threshold can be a simple number, such as at least 1, 2, 3, 4, 5, 6, 7, 8, 9, or 10 sequenced nucleic acid within the subset including the nucleotide variant or it can be a ratio, such as a least 0.5, 1, 2, 3, 4, 5, 10, 15, or 20 of sequenced nucleic acids within the subset include the nucleotide variant, among other possibilities. The comparison can be repeated for any designated position of interest in the reference sequence. Sometimes a comparison can be performed for designated positions occupying at least 20, 100, 200, or 300 contiguous positions on a reference sequence, e.g., 20-500, or 50-300 contiguous positions.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the disclosure can be used in combination with any other unless specifically indicated otherwise. Although the present disclosure has been described in some detail by way of illustration and example for purposes of clarity and understanding, it will be apparent that certain changes and modifications may be practiced within the scope of the appended claims.

What is claimed is:

1. A method for treating a subject having cancer associated with an ALK rearrangement, the method comprising:

(a) selecting the subject having cancer associated with ALK rearrangement, comprising:

generating a plurality of paired-end reads from cell-free nucleic acid molecules from a sample of the subject;

determining a plurality of paired-end reads from among the plurality of paired-end reads based on an overlap criterion;

determining a plurality of merged reads based on the plurality of paired-end reads that satisfy an overlapping criterion, wherein a merged read comprises a sequence based on respective sequences of paired-end reads;

determining a plurality of unmerged reads from among the plurality of paired-end reads that do not satisfy the overlap criterion, wherein a given unmerged read comprises a paired-end read that does not satisfy the overlap criterion with a mated paired-end read;

aligning the plurality of merged reads and the plurality of unmerged reads to a human reference genome to generate a plurality of aligned reads;

determining a plurality of split reads from among the plurality of aligned reads, wherein a given split read includes a first subsequence portion that aligns to a first nucleic acid locus of the reference sequence and a second subsequence portion that aligns to a second nucleic acid locus of the reference sequence, wherein the second nucleic acid locus is different from the first nucleic acid locus;

determining for a given split read, a breakpoint comprising a pair of genomic locations corresponding to the first nucleic acid locus and the second nucleic acid locus;

clustering the plurality of split reads based on their respective breakpoints to generate a plurality of variant clusters; and determining that one or more variant clusters meeting a predetermined criterion are indicative of an ALK rearrangement, thereby detecting an ALK rearrangement in the sample from the subject; and (b) administering a treatment comprising lorlatinib or crizotinib to the subject to treat the cancer based on the detected ALK rearrangement.

2. The method of claim 1, wherein a given unmerged read of the plurality of unmerged reads has a corresponding unmerged read, the method further comprising:

generating an artificial nucleotide sequence for a given unmerged read and corresponding unmerged read.

3. The method of claim 2, further comprising concatenating the artificial nucleotide sequence to a first sequence of the unmerged read and a second sequence of the corresponding unmerged read.

4. The method of claim 3, wherein the artificial nucleotide sequence is located between the first and second sequences.

5. The method of claim 2, wherein the artificial nucleotide sequence is at least 1 nucleotide, at least 2 nucleotides, at least 5 nucleotides, at least 10 nucleotides, at least 15 nucleotides, at least 20 nucleotides, at least 30 nucleotides, at least 40 nucleotides, at least 50 nucleotides, or at least 100 nucleotides in length.

6. The method of claim 2, wherein a location of a breakpoint is approximated to be located within the artificial nucleotide sequence.

7. The method of claim 1, wherein the respective breakpoints are no more than 5 nucleotides, no more than 10 nucleotides or no more than 25 nucleotides apart.

8. The method of claim 1, wherein the predetermined criterion comprises having more than one split read in any one or more of the plurality of variant clusters.

9. The method of claim 1, wherein the predetermined criterion comprises having at least one split read within any one or more of the plurality of variant clusters in which a breakpoint occurs within the first or the second subsequence.

10. A method for treating a subject having cancer associated with an ALK rearrangement, the method comprising:

(a) selecting the subject having cancer associated with ALK rearrangement, comprising:

generating a plurality of paired-end reads generated from cell-free nucleic acid molecules from a sample of the subject;

determining a plurality of merged reads based on respective mated pairs of paired-end reads that satisfy an overlap criterion, wherein a merged read comprises a sequence based on respective sequences of paired-end reads;

determining a plurality of unmerged reads from among the plurality of paired-end reads, wherein a given unmerged read comprises a paired-end read that does not satisfy an overlap criterion with a mated paired-end read;

generating a plurality of concatenated unmerged reads based on the plurality of unmerged reads;

aligning the plurality of merged reads and the plurality of concatenated unmerged reads to a human reference genome to generate a plurality of aligned reads;

determining a plurality of split reads from among the plurality of aligned reads, wherein a given split read from among the plurality of split reads includes a first subsequence portion that aligns to a first nucleic acid locus of the reference sequence and a second subsequence portion that aligns to a second nucleic acid locus of the reference sequence, the second nucleic acid locus different from the first nucleic acid locus; and determining that a plurality of split reads meeting a predetermined criterion comprise an ALK rearrangement, thereby detecting an ALK rearrangement in the sample from the subject; and (b) administering a treatment comprising a tyrosine kinase inhibitor to the subject based on the detected ALK rearrangement.

11. The method of claim 10, further comprising:

determining a plurality of merged split reads from among the plurality of split reads that originated from the plurality of merged reads;

generating, a plurality of variant clusters based on the plurality of merged split reads; and determining pairs of breakpoints for the plurality of variant clusters, wherein a given pair of breakpoints comprises a first breakpoint corresponding to a corresponding first nucleic acid locus and a second breakpoint corresponding to a corresponding second nucleic acid locus, wherein breakpoints meeting a predetermined criterion comprise an ALK rearrangement, thereby detecting an ALK rearrangement from the determined pairs of breakpoints.

12. The method of claim 11, further comprising:

determining one or more of the plurality of variant clusters that meet a criterion as indicative of an ALK rearrangement.

13. The method of claim 12, further comprising:

determining a plurality of unmerged split reads from among the plurality of split reads that originated from the plurality of unmerged reads; and determining that an unmerged split read aligns to the first nucleic acid locus and the second nucleic acid locus, wherein the alignment of the unmerged split read to the first nucleic acid locus and the second nucleic acid locus is used as the criterion.

14. The method of claim 12, wherein the predetermined criterion comprises having more than one split read in one or more of the plurality of variant clusters.

15. The method of claim 12, wherein the predetermined criterion comprises having at least one split read within one or more of the plurality of variant clusters in which a breakpoint occurs within the first or the second subsequence.

16. The method of claim 11, wherein generating the plurality of variant clusters is based further on one or more of the plurality of concatenated unmerged reads flanking a merged read.

17. The method of claim 10, the method further comprising:

determining a plurality of unmerged split reads from among the plurality of split reads that originated from the plurality of unmerged reads;

generating a plurality of variant clusters based on the plurality of unmerged split reads; and determining pairs of breakpoints for a given one of the plurality of variant clusters, wherein a given pair of breakpoints comprises a first breakpoint corresponding to a corresponding first nucleic acid locus and a second breakpoint corresponding to a corresponding second nucleic acid locus.

18. The method of claim 10, further comprising:

generating a plurality of variant clusters based on the plurality of split reads; and determining pairs of breakpoints for a given one of the plurality of variant clusters, wherein a given pair of breakpoints comprises a first breakpoint corresponding to a corresponding first nucleic acid locus and a second breakpoint corresponding to a corresponding second nucleic acid locus.

19. The method of claim 10, wherein the tyrosine kinase inhibitor comprises lorlatinib or crizotinib.

* * * * *